(12) United States Patent
Slishman

(10) Patent No.: US 10,517,750 B2
(45) Date of Patent: Dec. 31, 2019

(54) TRACTION SPLINTS AND METHODS OF USING TRACTION SPLINTS

(71) Applicant: Tri-Tech Forensics, Inc., Leland, NC (US)

(72) Inventor: Samuel Slishman, San Luis Obispo, CA (US)

(73) Assignee: Tri-Tech Forensics, Inc., Leland, NC (US)

( * ) Notice: Subject to any disclaimer, the term of this patent is extended or adjusted under 35 U.S.C. 154(b) by 896 days.

(21) Appl. No.: 14/949,569

(22) Filed: Nov. 23, 2015

(65) Prior Publication Data

US 2016/0151192 A1 Jun. 2, 2016

Related U.S. Application Data

(60) Provisional application No. 62/086,509, filed on Dec. 2, 2014.

(51) Int. Cl.
*A61F 5/00* (2006.01)
*A61F 5/048* (2006.01)
*A61F 5/058* (2006.01)

(52) U.S. Cl.
CPC .......... *A61F 5/048* (2013.01); *A61F 5/05841* (2013.01)

(58) Field of Classification Search
CPC .. A61F 5/048; A61F 5/042; A61F 5/04; A61F 5/05841; A61F 5/01; A61F 5/058; A61F 5/00; A61F 5/0585; A61F 5/0102; A61F 5/05858; A61F 5/05866;

(Continued)

(56) References Cited

U.S. PATENT DOCUMENTS

| | | |
|---|---|---|
| 82,478 A | 9/1868 | Ballard |
| 350,526 A | 10/1886 | Bunce |
| 655,671 A | 8/1900 | Crooker et al. |

(Continued)

OTHER PUBLICATIONS

"MTS: Mustang Traction Splint," Emergency Products and Research, available at least as early as Jun. 2014. Product information webpage downloaded from http://www.epandr.com/products/traction/mts.php.

(Continued)

*Primary Examiner* — Victoria J Hicks
(74) *Attorney, Agent, or Firm* — DASCENZO Intellectual Property Law P.C.

(57) ABSTRACT

Portable traction splints and methods of use in applying traction to an injured patient's limb, or limbs, are disclosed. The disclosed traction splints may be extendable from a collapsed configuration adapted for transportation and storage towards an extended configuration adapted for applying traction to an injured patient, using telescoping members. One or more straps may be provided for securing the traction splint to the patient. One or more of such straps may include a tourniquet portion and/or may be selectively oriented in different directions relative to the telescoping members. The disclosed traction splints may include a traction mechanism that utilizes a mechanical advantage in applying traction to the patient's limb. Such traction mechanisms may have a traction cord path that utilizes the same hardware as an adjustment mechanism that selectively allows or prevents one of the telescoping members from moving with respect to another.

24 Claims, 12 Drawing Sheets

(58) Field of Classification Search
CPC .... A61F 5/05875; A61F 5/0118; A61F 5/013; A61F 5/0104; A63B 2023/006
See application file for complete search history.

(56) References Cited

U.S. PATENT DOCUMENTS

| | | | |
|---|---|---|---|
| 739,200 A | 9/1903 | Moore | |
| 1,605,578 A | 11/1926 | Clark | |
| 2,058,563 A | 10/1936 | Campbell | |
| 2,186,456 A | 1/1940 | Gordon | |
| 2,252,258 A | 8/1941 | Hayden | |
| 2,260,216 A | 10/1941 | Doyle | |
| 2,269,065 A | 1/1942 | Roberts | |
| 2,398,247 A | 11/1944 | Redcliffe | |
| 2,377,940 A | 6/1945 | Hughes | |
| 2,394,653 A | 2/1946 | Auerhaan | |
| 3,299,888 A | 1/1967 | Muchinhaupt | |
| 3,413,971 A | 12/1968 | Evans | |
| 3,454,002 A | 7/1969 | Westlake et al. | |
| 3,503,390 A | 3/1970 | Peters | |
| 3,556,090 A | 1/1971 | Viel | |
| 3,750,659 A | 8/1973 | Loomans | |
| 3,756,227 A | 9/1973 | Sager | |
| 3,785,371 A | 1/1974 | Lewis | |
| 3,888,243 A | 6/1975 | Powlan | |
| 3,942,521 A | 3/1976 | Klippel | |
| 3,981,500 A | 9/1976 | Ryan | |
| 4,407,277 A * | 10/1983 | Ellison | A61F 5/04 128/882 |
| 4,409,971 A | 10/1983 | Guerriero | |
| 4,485,808 A | 12/1984 | Hepburn | |
| 4,531,514 A | 7/1985 | McDonald et al. | |
| 4,570,621 A | 2/1986 | Guerriero | |
| 4,585,363 A * | 4/1986 | McGuire | A61F 5/00 401/48 |
| 4,608,971 A | 9/1986 | Borschneck | |
| 4,641,637 A | 2/1987 | Rosen | |
| 4,649,907 A | 3/1987 | Whitehead et al. | |
| 4,708,131 A | 11/1987 | Kendrick | |
| 4,729,453 A | 3/1988 | Lyons, Sr. | |
| 4,750,479 A | 6/1988 | Schawl | |
| 4,809,725 A | 3/1989 | Champigny | |
| 4,830,365 A | 5/1989 | March | |
| 4,911,152 A | 3/1990 | Barnes et al. | |
| 5,019,077 A | 5/1991 | De Bastiani et al. | |
| 5,071,119 A | 12/1991 | Johnson | |
| 5,121,753 A * | 6/1992 | Paez | A61B 5/103 33/515 |
| 5,181,904 A | 1/1993 | Cook et al. | |
| 5,230,700 A | 7/1993 | Humbert et al. | |
| 5,303,716 A | 4/1994 | Mason et al. | |
| 5,328,433 A | 7/1994 | Berman | |
| 5,342,288 A | 8/1994 | Lee et al. | |
| 5,387,186 A | 2/1995 | Edland | |
| 5,403,350 A | 4/1995 | McAtee | |
| 5,441,307 A | 8/1995 | Quintana et al. | |
| 5,636,650 A | 6/1997 | Kroeze | |
| 5,681,272 A | 10/1997 | Lee | |
| 5,755,245 A | 5/1998 | Van Helvoort | |
| 5,769,104 A | 6/1998 | Uemura | |
| 5,775,334 A | 7/1998 | Lamb et al. | |
| 5,778,914 A | 7/1998 | Trani | |
| 5,807,294 A | 9/1998 | Cawley et al. | |
| 5,944,677 A | 8/1999 | Richard | |
| 5,957,477 A | 9/1999 | Ensz et al. | |
| 5,996,602 A | 12/1999 | Cato, III | |
| 6,082,767 A | 7/2000 | Bujold et al. | |
| 6,085,766 A | 7/2000 | Geary | |
| 6,126,623 A | 10/2000 | Seay, III | |
| 6,190,345 B1 | 2/2001 | Henderson | |
| 6,394,972 B1 * | 5/2002 | Slishman | A45B 9/00 602/32 |
| 6,402,668 B1 | 6/2002 | Harker | |
| 6,443,918 B1 | 9/2002 | Wang | |
| 6,669,659 B2 | 12/2003 | Dittmer et al. | |
| 6,786,882 B2 * | 9/2004 | Slishman | A45B 9/00 602/32 |
| 6,913,587 B2 | 7/2005 | Slishman | |
| 8,273,044 B1 * | 9/2012 | Larson | A61F 5/048 128/882 |
| 8,870,802 B1 | 10/2014 | Anderson et al. | |
| 2003/0050588 A1 * | 3/2003 | Slishman | A45B 9/00 602/32 |
| 2004/0167450 A1 | 8/2004 | Buckman et al. | |
| 2005/0240136 A1 * | 10/2005 | Price | A61F 5/04 602/32 |
| 2006/0009767 A1 | 1/2006 | Kiester | |
| 2011/0066095 A1 * | 3/2011 | Price | A61F 5/0106 602/16 |
| 2012/0215254 A1 | 8/2012 | Brub | |

OTHER PUBLICATIONS

"CT-6 Leg Splint Visual User Guide," FareTec Inc, 2010. Downloaded from http://www.faretec.com/images/p.%201small.jpg and http://www.faretec.com/images/p.%202small.jpg.

* cited by examiner

TRACTION SPLINTS AND METHODS OF USING TRACTION SPLINTS

RELATED APPLICATION

This application claims priority to U.S. Provisional Patent Application Ser. No. 62/086,509, which was filed on Dec. 2, 2014, the complete disclosure of which is hereby incorporated by reference for all purposes.

FIELD

The present disclosure is directed generally to traction splints and methods of using traction splints.

BACKGROUND

Traction splints are portable devices that provide external traction to an injured limb. Traction splints often are used as pre-hospital care to stabilize an injured or fractured limb so that the injured patient may be transported more easily and safely to a hospital or other care facility. Portable traction splints may have utility in many applications, such as military (e.g., battlefield injuries), emergency response, wilderness first aid, and the like. Traction splints may be used to stabilize leg injuries, such as suspected or actual fractures of the femur, tibia, or fibula, as well as upper and lower arm injuries (e.g., fractures to the humerus, radius, or ulna). Generally, a traction splint includes one or more straps that are used to secure the injured limb to an elongate support, and a mechanical device to apply traction to the injured limb. Examples of conventional traction splints are disclosed in U.S. Pat. Nos. 6,913,587, 6,786,882, and 6,394,972 to Slishman, the complete disclosures of which are hereby incorporated by reference for all purposes.

DETAILED DESCRIPTION

Figure 1:
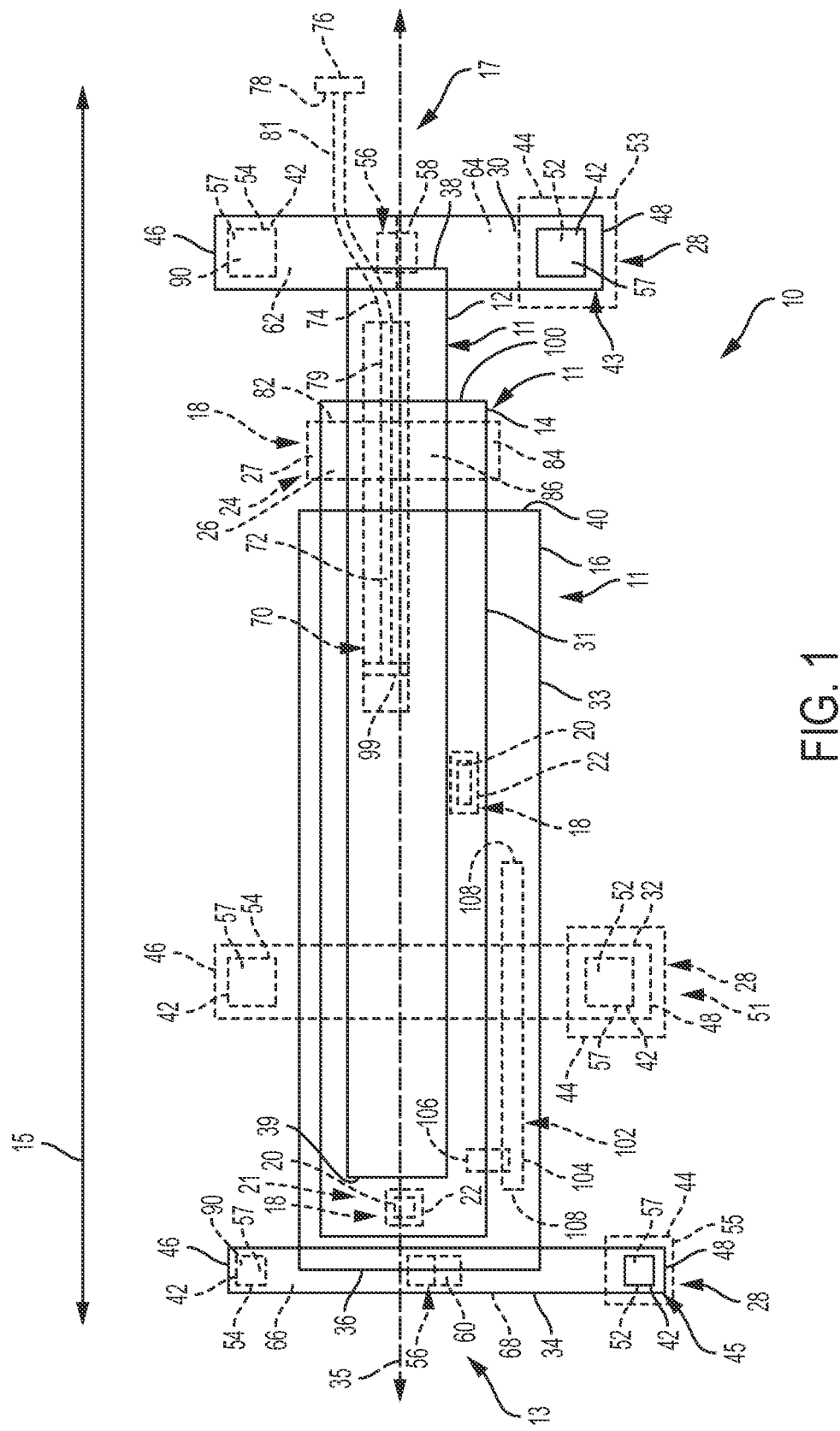
FIG. 1 is a schematic representation of examples of a traction splint according to the present disclosure.

FIGS. 1-12 provide examples of traction splints 10 according to the present disclosure, components of such traction splints, and/or methods of using such fraction splints. Elements that serve a similar, or at least substantially similar, purpose are labeled with like numbers in each of FIGS. 1-12, and these elements may not be discussed in detail herein with reference to each of FIGS. 1-12. Similarly, all elements may not be labeled in each of FIGS. 1-12, but reference numerals associated therewith may be utilized herein for consistency. Elements, components, and/or features that are discussed herein with reference to one or more of FIGS. 1-12 may be included in and/or utilized with any of FIGS. 1-12 without departing from the scope of the present disclosure.

In general, elements that are likely to be included in a given (i.e., a particular) example are illustrated in solid lines, while elements that are optional to a given example are illustrated in dashed lines. However, elements that are shown in solid lines are not essential to all embodiments, and an element shown in solid lines may be omitted from a particular embodiment without departing from the scope of the present disclosure.

FIG. 1 provides a schematic representation of examples of traction splints 10 according to the present disclosure. Generally, traction splint 10 may include a plurality of interconnected elongate members 11 that are selectively configured, or positioned, between a collapsed, or stowed, configuration of the traction splint and an extended, or use, configuration of the traction splint. One or more adjustment mechanisms 18 may be configured to selectively allow or restrict movement of a respective elongate member 11 with respect to another elongate member 11 to selectively and reversibly extend and/or collapse traction splint 10 between the collapsed and extended configurations. In the collapsed configuration, a proximal end region 17 of traction splint 10 may be located a first distance from a distal end region 13 of traction splint 10, and in the extended configuration, proximal end region 17 of traction splint 10 may be located a second distance from distal end region 13 of traction splint 10, the second distance being greater than the first distance. One or more straps 28, such as a proximal strap 30 adjacent a proximal end region 17 of fraction splint 10, a middle strap 32, and/or a distal strap 34 adjacent a distal end region 13 of traction splint 10, may be coupled to traction splint 10 and configured to secure traction splint 10 to a patient's limb or limbs. Traction splint 10 may include a traction mechanism 70 that is configured to apply traction to the patient's limb such that respective elongate members 11 (e.g., an inner member 12 and an outer member 16) are pressed away from one another when a user applies a tension force to an external portion 81 of a traction cord 74 adjacent proximal end region 17 of traction splint 10.

In the following discussion, traction splint 10 is described and illustrated in the context of including a plurality of nesting, telescoping members that may collapse into each other for increased portability (e.g., the collapsed configuration) and which may adjustably extend outwardly from each other when in use (e.g., towards the extended configuration). For example, inner member 12 may be at least partially nested, or positioned within, a middle member 14, which may in turn be positioned at least partially within outer member 16 (e.g., at least a portion of middle member 14 may be positioned between inner member 12 and outer member 16). Traction splint 10 may be configured to be selectively and reversibly extended towards the extended configuration by sliding inner member 12 in a longitudinal direction (e.g., in the directions indicated by arrow 15) with respect to middle member 14 and/or outer member 16. For example, inner member 12 may be configured to be selectively longitudinally slid with respect to middle member 14 (e.g., moved further into or out of middle member 14) to adjust the overall length of traction splint 10. Additionally or alternatively, middle member 14 may be configured to be selectively longitudinally slid with respect to outer member 16 (e.g., moved further into or out of outer member 16) to adjust the overall length of traction splint 10. Traction splint 10 may be configured to be at least temporarily retained in a configuration between the collapsed configuration and the extended configuration, inclusive. For example, adjustment mechanism 18 may be configured to selectively temporarily retain traction splint 10 in the collapsed configuration, in the extended configuration, or at any desired and/or predetermined length in between, as desired.

In FIG. 1, traction splint 10 is shown including three telescoping members, namely, inner member 12, middle member 14, and outer member 16. It is within the scope of the present disclosure that traction splint 10 may include only two elongate members 11 (e.g., inner member 12 and outer member 16) or more than three elongate members 11 (e.g., inner member 12, two or more middle members 14, and outer member 16). Traction splint 10 may be adjustable to a plurality of different extended configurations (e.g., may be selectively and reversibly adjustable to a plurality of different lengths) so that it may be appropriately sized for use on a variety of sizes of patients (e.g., adults and pediatric patients) as well as for use with a variety of different limbs (e.g., the same traction splint 10 may be configurable for use on both upper limb injuries and lower limb injuries). Once extended from the collapsed configuration towards the extended configuration, to the desired length, traction splint 10 may be configured to be immediately ready for securement to the patient's limb, without further assembly.

The plurality of elongate members 11 may be coupled together or otherwise interconnected via any suitable mechanism that enables this selective and reversible positioning of the members between the collapsed and extended configurations of the traction splint. As examples, the plurality of elongate members 11 may include telescoping members that nest at least partially within each other, hinged members that are interconnected by hinges, and/or clamped members that are selectively clamped, or otherwise fastened together. In some examples, the elongate members 11 are at least substantially non-rotatable about a longitudinal axis 35 with respect to each other. For example, inner member 12 may be at least substantially non-rotatable with respect to middle member 14 and/or outer member 16. Additionally or alternatively, middle member 14 may be at least substantially non-rotatable with respect to outer member 16.

Traction splint 10 may include a plurality of adjustment mechanisms 18 that may be configured to adjust the length of traction splint 10. For example, adjustment mechanisms 18 may include a first adjustment mechanism 24 and a second adjustment mechanism 21, but traction splints 10 according to the present disclosure may include more or fewer adjustment mechanisms 18. First adjustment mechanism 24 may be configured to selectively and reversibly allow movement (e.g., at least substantially longitudinal movement along arrow 15) of inner member 12 with respect to middle member 14 and/or with respect to outer member 16. Second adjustment mechanism 21 may be configured to selectively and reversibly allow movement (e.g., at least substantially longitudinal movement along arrow 15) of middle member 14 with respect to outer member 16.

First adjustment mechanism 24 may generally function as clamp, wherein tightening of the clamp may be configured to prevent movement of inner member 12 with respect to middle member 14 and/or outer member 16. In some examples, a post 26 may be positioned to extend through inner member 12 and/or outer member 16. Post 26 may, for example, be coupled to middle member 14 adjacent a proximal end 100 of middle member 14. A flange or head portion 84 of post 26 may be positioned adjacent an outer surface 31 of middle member 14 (or adjacent an outer surface 33 of outer member 16, in examples without a middle member 14), and a threaded portion 82 of post 26 may extend adjacent outer surface 31 of middle member 14, opposite head portion 84. In some examples, post 26 may be threaded along substantially its entire length. In some examples, post 26 may be threaded along just a portion of its length. In some examples, first adjustment mechanism 24 may include a hollow shaft 86 positioned within inner member 12 and middle member 14, such that post 26 extends through inner member 12 and middle member 14 via hollow shaft 86.

A nut portion 27 may be coupled to threaded portion 82 such that tightening nut portion 27 relative to threaded portion 82 of post 26 is configured to prevent movement of inner member 12 with respect to middle member 14 (or with respect to outer member 16 in examples without middle member 14). For example, nut portion 27 may be threaded onto threaded portion 82 of post 26 until head portion 84 and nut portion 27 together clamp middle member 14 and at least substantially prevent longitudinal movement of inner member 12 with respect to middle member 14 (or outer member 16). Selective loosening of nut portion 27 relative to threaded portion 82 may allow movement of inner member 12 with respect to middle member 14 (or outer member 16), for adjustment of the length of traction splint 10. The farther that inner member 12 is extended out from within middle member 14 (or outer member 16), the longer the length of traction splint 10 as it is moved toward its extended configuration. Similarly, the farther that inner member 12 is inserted into middle member 14 (or outer member 16), the shorter the overall length of traction splint 10 as it is moved toward its collapsed configuration.

Second adjustment mechanism 21 may include, for example, a plunger 20 that may be spring-biased and coupled to middle member 14, and a plurality of adjustment holes 22 formed in outer member 16. Plunger 20 may be spring-biased to extend through a respective one of the plurality of adjustment holes 22 when plunger 20 is not depressed. Traction splint 10 may be configured to be extended towards the extended configuration by depressing plunger 20 and sliding middle member 14 longitudinally with respect to outer member 16 until middle member 14 is positioned such that plunger 20 extends through the desired respective adjustment hole 22 of outer member 16.

When plunger 20 extends through a respective adjustment hole 22, middle member 14 may be substantially prevented from moving with respect to outer member 16. In order to adjust middle member 14 with respect to outer member 16, plunger 20 may be pushed radially inward through the current respective adjustment hole 22 through which plunger 20 is positioned, in order to permit longitudinal movement of middle member 14 with respect to outer member 16. As middle member 14 is moved (e.g., longitudinally slid in and/or out of outer member 16), plunger 20 may be moved toward a concentric position within a different respective adjustment hole 22. Once plunger 20 is positioned substantially concentrically to the different respective adjustment hole, plunger 20 may, due to its spring bias, be configured to automatically extend through the different respective adjustment hole 22, thereby locking middle member 14 into a new position with respect to outer member 16. If it is desired to move middle member 14 further, plunger 20 again may be pushed radially inward through the respective adjustment hole 22 in order to permit further movement of middle member 14 relative to outer member 16.

Outer member 16 may include a plurality of adjustment holes 22 spaced along the length of outer member 16, to allow traction splint 10 to be adjusted to a plurality of overall lengths. The number of adjustment holes 22 may vary, such as to define a corresponding number of predefined adjustment positions, or lengths, of the traction splint 10 and/or its elongate members 11. For example, outer member 16 may include two or more, three or more, four or more, five or more, six or more, seven or more, eight or more, nine or more, and/or ten or more spaced-apart adjustment holes 22. The farther that middle member 14 is extended out from within outer member 16, the longer the length of traction splint 10. Similarly, the farther that middle member 14 is pushed into outer member 16, the shorter the overall length of traction splint 10, as it is moved towards its collapsed configuration.

Second adjustment mechanism 21 may thus be configured to selectively and reversibly allow adjustment of and retain the position of middle member 14 with respect to outer member 16 without relying on friction between the respective members. Some conventional adjustable splints utilize an extension mechanism that involves twisting the members with respect to one another, and relies on friction to retain the extended position. These conventional adjustable splints may be subject to unintentional loosening during use. Adjustment mechanisms 18 of the present disclosure, such as second adjustment mechanism 21, may be configured to prevent such unintentional loosening, as plunger 20 may be configured to prevent further longitudinal sliding of middle member 14, in either direction, with respect to outer member 16 until plunger 20 is depressed.

The previously described plunger 20, adjustment holes 22, and post 26 with head portion 84 and nut portion 27 are but two examples of suitable adjustment mechanisms 18 that may be used to selectively secure elongate members 11 of traction splint 10 relative to one another to position traction splint 10 in a selected configuration. It is within the scope of the present disclosure that any suitable mechanism and/or structure, including spring-biased mechanisms, friction-lock mechanisms, cam mechanisms, and the like, may be utilized as adjustment mechanisms 18 (e.g., as first adjustment mechanism 24 and/or second adjustment mechanism 21). Further, the same or different types of adjustment mechanisms 18 may be utilized to selectively position inner member 12 with respect to middle member 14, and/or to position middle member 14 with respect to outer member 16. For example, a respective post 26, head portion 84, and nut portion 27 also may be utilized to secure middle member 14 with respect to outer member 16.

Some examples of traction splints 10 according to the present disclosure may include an anti-rotation feature 102 that is configured to prevent rotation of middle member 14 with respect to outer member 16 as middle member 14 is moved longitudinally with respect to outer member 16. Anti-rotation feature 102 also may be configured to prevent rotation of middle member 14 with respect to outer member 16 when middle member 14 is secured or locked into a longitudinal position (e.g., when traction splint 10 is at least partially extended towards the extended configuration) with respect to outer member 16.

Additionally or alternatively, anti-rotation feature 102 may be configured to prevent separation of middle member 14 from outer member 16 (e.g., anti-rotation feature 102 may serve as a stop, to prevent middle member 14 from extending too far with respect to outer member 16, thereby preventing middle member 14 from extending completely out of outer member 16 as traction splint 10 is extended towards the extended configuration). Anti-rotation feature 102 additionally or alternatively may be referred to as an anti-rotation mechanism 102 and/or as an anti-separation mechanism 102.

For example, anti-rotation feature 102 may include a longitudinally-extending slot 104 formed in outer member 16, and a pin 106 coupled to middle member 14 (or inner member 12, in examples without a middle member 14), such that pin 106 is positioned to extend at least partially, and optionally completely, through longitudinally-extending slot 104 of outer member 16. In some examples, pin 106 may be formed integrally with middle member 14 (or formed integrally with inner member 12). Pin 106 may be configured to travel longitudinally along longitudinally-extending slot 104 as middle member 14 (or inner member 12) is moved with respect to outer member 16. Longitudinally-extending slot 104 and pin 106 may be sized and shaped relative to each other such that pin 106 allows little to no circumferential rotation of middle member 14 with respect to outer member 16, about longitudinal axis 35. For example, the diameter (or other dimension) of pin 106 may be only slightly smaller than the width of longitudinally-extending slot 104 in some examples. Because pin 106 may be coupled to middle member 14, as middle member 14 is longitudinally moved with respect to outer member 16, pin 106 also moves longitudinally with respect to outer member 16, and therefore travels along longitudinally-extending slot 104. Longitudinally-extending slot 104 may therefore serve as a track, or race, setting the circumferential orientation of middle member 14 with respect to outer member 16. Ends 108 of longitudinally-extending slot 104 may be positioned to prevent middle member 14 from extending too far out of or too far into outer member 16. For example, when middle member 14 is moved in a given direction with respect to outer member 16 such that pin 106 reaches either respective end 108 of longitudinally-extending slot 104, such interaction of pin 106 with the respective end 108 may prevent further movement of middle member 14 with respect to outer member 16 in that direction.

As discussed, traction splint 10 may include a plurality of straps 28 that are configured to secure traction splint 10 to a patient's limb. For example, the plurality of straps may include proximal strap 30, middle strap 32, and/or distal strap 34, with each strap 28 being coupled to one or more respective elongate members 11 of traction splint 10. Distal strap 34 may be coupled, for example, to outer member 16 adjacent distal end region 13 of traction splint 10, such as adjacent a distal end 36 of outer member 16. Proximal strap 30 may be coupled, for example, to inner member 12 adjacent proximal end region 17 of traction splint 10, such as adjacent a proximal end 38 of inner member 12. In this manner, straps 28 may be positioned and secured to traction splint 10 such that straps 28 do not interfere with movement of elongate members 11 while extending fraction splint 10 towards an extended configuration.

Middle strap 32 may be coupled to outer member 16, typically positioned between distal end 36 of outer member 16 and a proximal end 40 of outer member 16. Middle strap 32 may be slidably arranged on outer member 16, such that middle strap 32 may be adjustable to be positioned substantially anywhere along the length of outer member 16 (e.g., middle strap 32 may be configured to be selectively moved in a longitudinal direction with respect to inner member 12 and outer member 16). Middle strap 32 may be used to provide additional support to the fraction splint 10 and/or a patient's injured limb to which the traction splint is secured. Middle strap 32 may be configured to assist in restricting relative rotation and/or axial adjustment of traction splint 10 on a patient's limb, and as such may be described as providing, or increasing, rotational stability or rotational positioning of traction splint 10 on the patient's limb. In some examples, middle strap 32 may be selectively removable from traction splint 10. For example, in certain applications, middle strap 32 may be unnecessary in securing traction splint 10 to a patient, and thus may be removed. Middle strap 32 optionally may be utilized as a carry strap, a belt, and/or for lifting, including lifting of an injured individual. Some examples of traction splints 10 may include only proximal strap 30 and distal strap 34, without middle strap 32.

In some examples, each of straps 28 may be color-coded in order to aid users in applying traction splint 10 to a patient. For example, proximal strap 30 may be a first color, middle strap 32 may be a second color, and/or distal strap 34 may be a third color, where none of the first, second, and third colors are the same. Use of color-coded straps 28 may aid users in correctly orienting fraction splint 10 and more easily identifying, for example, which of straps 28 is proximal strap 30 and which of straps 28 is distal strap 34. Additionally or alternatively, other identifying features may be included to aid in distinguishing the respective straps 28 from one another, such as the use of colored portions, stripes, different materials, tags, markings, labels, and/or different colored strap fasteners 42 secured to different respective straps 28.

In some examples, proximal strap 30 may include a rubberized portion and/or a coating, such as including a plurality of embedded elastic fibers integrated into proximal strap 30. Such a rubberized portion may, in some examples, impart some elasticity to at least a portion of proximal strap 30, such that it is configured to resiliently stretch in response to application of a sufficient tensile force. Additionally or alternatively, the rubberized portion or coating may be configured to increase friction, thereby improving grip when secured to a patient's limb and restricting rotation or other adjustment of the strap after the strap is secured around the patient's limb. Similarly, in some examples, distal strap 34 may include a rubberized portion and/or a coating, such as including a plurality of embedded elastic fibers integrated into distal strap 34. Such a rubberized portion may, in some examples, impart some elasticity to at least a portion of distal strap 34, such that it is configured to resiliently stretch in response to application of a sufficient tensile force.

Additionally or alternatively, the rubberized portion or coating may be configured to increase friction, thereby improving grip when secured to a patient's limb, as discussed.

Proximal strap 30 and distal strap 34 may be moveably coupled to inner member 12 and outer member 16, respectively, using a respective strap connector 56. For example, a proximal strap connector 58 may be configured to couple proximal strap 30 to inner member 12, and a distal strap connector 60 may be configured to couple distal strap 34 to outer member 16. Each strap connector 56 may be configured to allow free rotation or other movement of the respective strap 28 (e.g., the entire respective strap 28 and/or the entire respective strap fastener 42) relative to the respective elongate member 11 to which the strap is coupled. In other words, proximal strap 30 may be configured to rotate about the point where it is secured to inner member 12 (e.g., about proximal strap connector 58), and/or distal strap 34 may be configured to rotate about the point where it is secured to outer member 16 (e.g., about distal strap connector 60). This rotation of the strap 28 relative to the corresponding elongate member 11 may include rotation of the entire strap 28 around and/or about the elongate member. In this manner, traction splint 10 may be configured to be selectively used in a right-limb orientation or in a left-limb orientation, in which one or more respective straps 28 are in a different position with respect to elongate members 11 in one orientation than in the other. As examples, the left-limb and right-limb orientations may correspond to orientations in which the straps secure traction splint 10 with the members (12, 14, 16) against a corresponding portion of the patient's limb, such as an anterior portion, a posterior portion, a medial portion, or a lateral portion.

In some examples, proximal strap 30 may be configured to be selectively rotated with respect to inner member 12 such that proximal strap 30 is rotatable in a plane that is at least substantially perpendicular to a cross-sectional plane defined by the cross-sectional area of inner member 12. For example, proximal strap 30 may be configured to be selectively rotated with respect to inner member 12 by at least 90 degrees, at least 180 degrees, and/or at least 360 degrees in the plane. In some examples, the entirety of proximal strap 30 may be configured to be selectively rotated with respect to inner member 12. In some examples, a region of proximal strap 30 that is coupled to inner member 12 may be configured to be selectively rotated with respect to inner member 12.

Additionally or alternatively, distal strap 34 may be configured to be selectively rotated with respect to outer member 16 such that distal strap 34 is rotatable in a plane that is at least substantially perpendicular to a cross-sectional plane defined by the cross-sectional area of outer member 16. For example, distal strap 34 may be configured to be selectively rotated with respect to outer member 16 by at least 90 degrees, at least 180 degrees, and/or at least 360 degrees in the plane. In some examples, the entirety of distal strap 34 may be configured to be selectively rotated with respect to outer member 16. In some examples, a region of distal strap 34 that is coupled to outer member 16 may be configured to be selectively rotated with respect to outer member 16.

Strap connectors 56 (e.g., proximal strap connector 58 and distal strap connector 60) may each comprise one or more fasteners, or fastening components, such as one or more pins, grommets, eyelets, rivets, and/or bolts. Some strap connectors 56 may include at least a first fastening component and a second fastening component, where one of the fastening components is substantially stationary with respect to a respective elongate member 11, while the other of the fastening components is configured to selectively rotate about the first.

In some examples, respective straps 28 may be configured such that respective free ends 46 may be rotated and/or oriented independently of respective terminal ends 48. For example, proximal strap 30 may be formed by a proximal first strap portion 62 and a proximal second strap portion 64 that are separate from one another (e.g., proximal strap 30 may be formed by two distinct proximal straps or strap segments) and are free to articulate or rotate independent of each other, about proximal strap connector 58. Proximal first strap portion 62 may extend from free end 46 of proximal strap 30 to a second end adjacent proximal strap connector 58. Proximal second strap portion 64 may extend from terminal end 48 of proximal strap 30 to a second end adjacent proximal strap connector 58. Additionally or alternatively, distal strap 34 may be formed by a distal first strap portion 66 and a distal second strap portion 68 that are separate from one another (e.g., distal strap 34 may be formed by two distinct distal straps or strap segments) and are free to articulate or rotate independent of each other, about distal strap connector 60. Distal first strap portion 66 may extend from free end 46 of distal strap 34 to a second end adjacent distal strap connector 60. Distal second strap portion 68 may extend from terminal end 48 of distal strap 34 to a second end adjacent distal strap connector 60.

To secure traction splint 10 to a patient's limb or limbs, one or more of proximal strap 30, middle strap 32, and distal strap 34 may include a respective strap fastener 42. For example, proximal strap 30 may include a proximal strap fastener 43 and distal strap 34 may include a distal strap fastener 45, each of which may be an example of strap fastener 42. Proximal strap fastener 43 may be configured to secure proximal strap 30 around the patient's limb such that proximal strap 30 forms a proximal loop 47 (seen in FIG. 3) around the patient's limb when proximal strap fastener 43 is engaged. In this manner, proximal strap 30 may be configured to secure traction splint 10 (e.g., inner member 12 of traction splint 10) to the patient's limb adjacent proximal end region 17 of traction splint 10. Similarly, distal strap fastener 45 may be configured to secure distal strap 34 around the patient's limb such that distal strap 34 forms a distal loop 49 (seen in FIG. 2) around the patient's limb when distal strap fastener 45 is engaged. In this manner, distal strap 34 may be configured to secure traction splint 10 (e.g., outer member 16 of traction splint 10) to the patient's limb adjacent distal end region 13 of traction splint 10. In some examples, middle strap 32 may include a middle strap fastener 51 configured to secure middle strap 32 in a middle loop around the patient's limb.

The circumference of proximal loop 47 (FIG. 3) may be selectively increased and decreased. For example, a respective free end 46 of proximal strap 30 may extend away from traction splint 10 for a distance sufficient that proximal strap 30 may be wrapped around a patient's limb. Free end 46 of proximal strap 30 (or another portion of proximal strap 30) may engage with proximal strap fastener 43 adjacent terminal end 48 of proximal strap 30 to create proximal loop 47. Proximal strap fastener 43 may be configured for selective adjustment of the circumference of proximal loop 47, such as by pulling free end 46 through proximal strap fastener 43 to tighten proximal loop 47. Similarly, the circumference of distal loop 49 (FIG. 2) may be selectively increased and decreased. For example, a respective free end 46 of distal strap 34 may extend away from traction splint 10 for a distance sufficient that distal strap 34 may be wrapped around a patient's limb. Free end 46 of distal strap 34 (or another portion of distal strap 34) may engage with distal strap fastener 45 adjacent terminal end 48 of distal strap 34 to create distal loop 49. Distal strap fastener 45 may be configured for selective adjustment of the circumference of distal loop 49, such as by pulling free end 46 through distal strap fastener 45 to tighten distal loop 49.

Strap fasteners 42 may be configured to be selectively and reversibly rotated via the respective strap connector 56, depending on whether traction splint 10 is being used on a patient's right limb or left limb. For example, proximal strap fastener 43 may be configured to be selectively and reversibly rotated, via proximal strap connector 58, with respect to inner member 12 between a left-limb orientation and a right-limb orientation, wherein, in the right-limb orientation, traction splint 10 is configured for securement to a patient's right limb, and wherein, in the left-limb orientation, traction splint 10 is configured for securement to a patient's left limb. Additionally or alternatively, distal strap fastener 45 may be configured to be selectively and reversibly rotated, via distal strap connector 60, with respect to outer member 16 between the left-limb orientation and the right-limb orientation.

Strap fasteners 42 (e.g., proximal strap fastener 43, middle strap fastener 51, and/or distal strap fastener 45) may include any suitable fastener, such as one or more clips, buckles, clasps, buttons, snaps, D-rings, Velcro® portions, cam buckles, lever buckles, side-squeeze buckles, and/or any other type of fastener suitable to secure a respective strap 28 in a respective loop around a patient's limb. One or more strap fasteners 42 may include one or more respective ladderlock portions 57, which may allow each respective strap 28 to be tightened and may employ friction to retain the strap in a tightened position.

One or more strap fasteners 42 may be a one-part fastener (such as a cam buckle, lever buckle, or D-rings), such that a respective free end 46 of the strap 28 may be inserted into the strap fastener and pulled through until the strap is sufficiently taut around the patient's limb. In some examples, the one-part strap fastener may be closed (such as in the case of a cam or lever buckle) to secure the strap in position around the patient's limb. Additionally or alternatively, one or more strap fasteners 42 may be a two-part fastener, having a respective first fastener part 52 and a respective second fastener part 54 configured to engage with one another in order to secure the strap around the patient's limb.

In some such examples, first fastener part 52 may be positioned adjacent a respective terminal end 48 of the strap 28. Second fastener part 54 may be positioned elsewhere on the strap, such as adjacent a respective free end 46, or elsewhere along the length of the strap. In examples where strap fastener 42 is a two-part fastener, strap fastener 42 may be, for example, a side-release buckle (which also may be known as a side-squeeze buckle) having a female portion (e.g., first fastener part 52) and a male portion (e.g., second fastener part 54), such that the male portion is configured to be inserted within the female portion to secure the buckle, thereby securing the respective strap 28 in a respective loop around the patient's limb. When it is desired to release the loop and remove traction splint 10 from the patient's limb, respective strap fasteners 42 may be released, and respective straps 28 may be removed from the fasteners to undo the respective strap loops. For example, the sides of a side-squeeze buckle fastener may be squeezed to release the buckle and separate the male portion from the female portion.

One or more of proximal strap 30, middle strap 32, and distal strap 34 may include a pad, or padded portion, 44. For example, padded portion 44 may include a proximal padding portion 53 coupled to proximal strap 30 and/or a distal padding portion 55 coupled to distal strap 34. Padded portions 44 may be configured to be positioned between a respective strap fastener 42 and the patient's limb, so as to lessen discomfort that may be caused by strap fastener 42 being in direct contact with the patient's limb. For example, padded portions 44 may be configured to provide cushioning to the patient's limb. One or more respective straps 28 (or portions thereof) and/or one or more respective strap fasteners 42 (or portions thereof) may be coupled to a respective padded portion 44.

Respective padded portions 44 may extend along substantially the entire length of one or more of proximal strap 30, middle strap 32, and distal strap 34 in some examples. In other examples, a respective padded portion 44 may be present at just a portion of one or more of proximal strap 30, middle strap 32, and distal strap 34. Padded portion 44 may include cushioning and/or may comprise a softer, more flexible, more compressible, and/or more resilient material than other portions of the strap 28. In some examples, padded portion 44 may be located adjacent a respective terminal end 48 of a respective strap 28 and/or adjacent a respective strap fastener 42 of one or more of proximal strap 30, middle strap 32, and distal strap 34.

Once fraction splint 10 is secured to the patient's limb via strap fasteners 42, traction mechanism 70 may be engaged to apply traction such that inner member 12 and outer member 16 are pressed away from one another. Such traction may help to stabilize the patient's limb and/or reduce the patient's pain by applying tension in opposite directions and transmitting such fraction to the patient's limb via proximal strap 30 and distal strap 34. For example, when traction mechanism 70 is engaged, inner member 12 and outer member 16 may be pressed away from one another, which may cause the respective portion of the patient's limb to which proximal strap 30 is secured to be pressed away from the respective portion of the patient's limb to which distal strap 34 is secured. Traction splint 10 may be configured such that fraction mechanism 70 may be engaged adjacent proximal end region 17 of traction splint 10.

Traction mechanism 70 generally may include a pulley mechanism 72 contained within inner member 12, middle member 14, and/or outer member 16, and traction cord 74, which may be configured to engage traction mechanism 70. Traction cord 74 may include an internal portion 79 positioned at least partially within inner member 12, middle member 14, and/or outer member 16, where internal portion 79 may be coupled to and/or engaged with pulley mechanism 72. External portion 81 of traction cord 74 may extend from inner member 12, such as adjacent proximal end region 17 of traction splint 10. Proportions of traction cord 74 that are internal and external may change as traction splint 10 is extended towards the extended configuration and/or collapsed towards the collapsed configuration. For example, as inner member 12 is extended out from middle member 14, the length of internal portion 79 of traction cord 74 may decrease, and the length of external portion 81 may increase. As tension is released from external portion 81, the length of external portion 81 may decrease, and the length of internal portion 79 may increase. Traction mechanism 70 may be configured such that applying a tension force to external portion 81 of traction cord 74 (e.g., pulling external portion 81 of traction cord 74 away from proximal end region 17) causes traction splint 10 to apply traction (e.g., causes proximal end 38 of inner member 12 and distal end 36 of outer member 16 to move longitudinally further away from each other).

A stopper 76 may be coupled to external portion 81 of traction cord 74, such as to a free end 78 of external portion 81. Stopper 76 may be configured to serve as a handle for a user, such that pulling stopper 76 away from inner member 12 causes traction splint 10 to apply traction when secured to a patient's limb (e.g., stopper 76 may be easier to hold on to than the traction cord 74 itself). Stopper 76 thus additionally or alternatively may be referred to as a pull 76, a handle 76, and/or a hand grip 76. In some examples, stopper 76 may simply be a knob or elongated portion tied to or otherwise secured to free end 78 of traction cord 74, but other configurations are also possible. Additionally or alternatively, stopper 76 may be configured to limit the extent to which traction cord 74 may be drawn into inner member 12 as traction splint 10 is extended towards the extended configuration and/or collapsed towards the collapsed configuration. For example, stopper 76 may be configured to prevent free end 78 of traction cord 74 from being drawn into inner member 12, such as by being sized to be too large to enter inner member 12. Thus, as traction cord 74 is pulled into inner member 12 (e.g., as the length of external portion 81 is decreased, such as when fraction splint 10 is collapsed), stopper 76 may prevent at least a portion of traction cord 74 adjacent free end 78 of traction cord 74 from being drawn into inner member 12, by virtue of free end 78 being secured to stopper 76 and being prevented from entering inner member 12 due to the relative sizes of stopper 76 and inner member 12.

Figure 6:
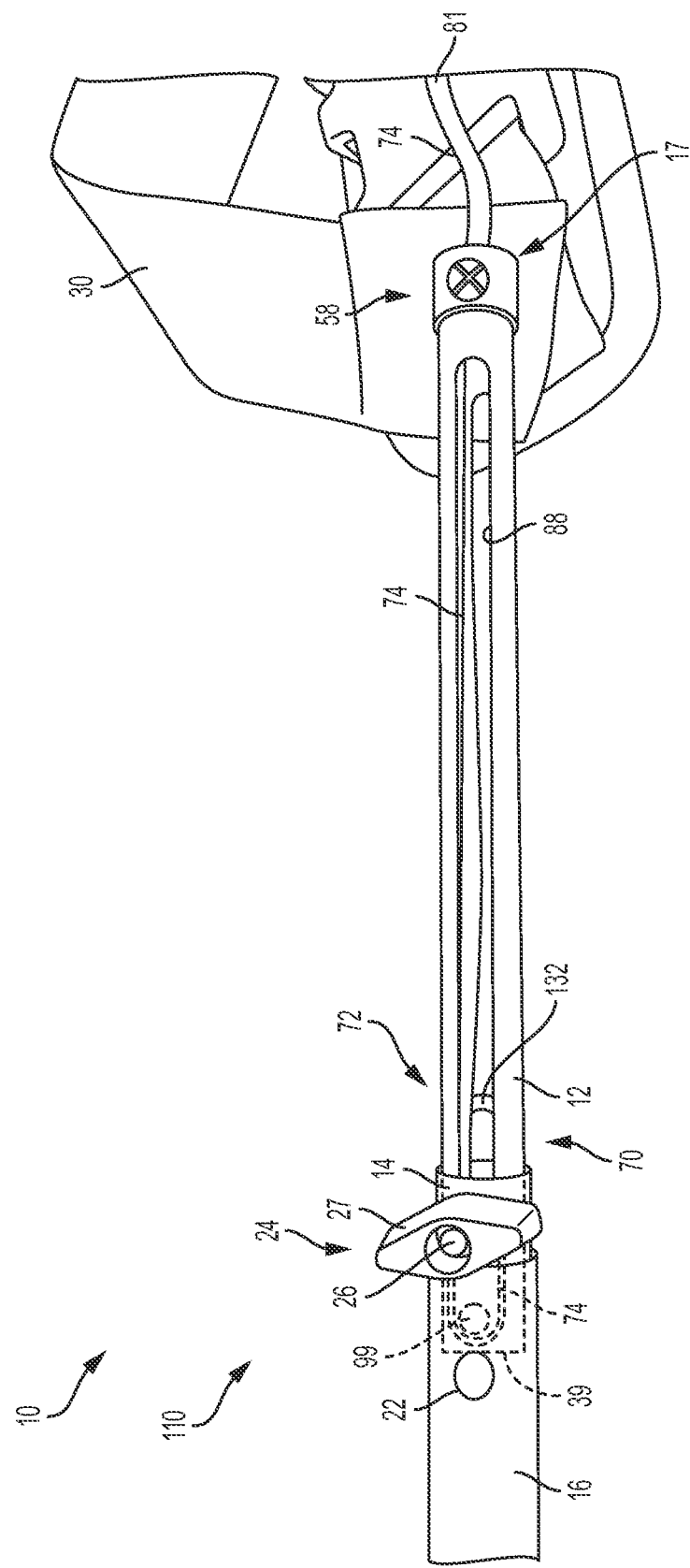
FIG. 6 is a top plan view of a portion of an example of a traction splint according to the present disclosure, showing an inner member and a proximal strap.

Internal portion 79 of traction cord 74 may be engaged with pulley mechanism 72, such that traction splint 10 has a mechanical advantage in applying traction to a patient's limb. For example, pulley mechanism 72 may include one or more structures positioned within inner member 12, middle member 14, and/or outer member 16, around which traction cord 74 may be wrapped, in order to create the pulley. In some examples, such structures may include a portion of a respective adjustment mechanism 18 (e.g., first adjustment mechanism 24) and an anchor pin 99 positioned within inner member 12, middle member 14, and/or outer member 16. In some examples, anchor pin 99 may be coupled to inner member 12, such as adjacent a distal end 39 of inner member 12 (FIG. 6). Traction cord 74 (e.g., internal portion 79 of fraction cord 74) may include an anchor loop 98 (FIGS. 7-8) that is anchored around anchor pin 99, with anchor loop 98 being adjacent the opposite end of traction cord 74 from free end 78. Pulley mechanism 72 may include a portion of first adjustment mechanism 24, such as post 26 and/or hollow shaft 86. For example, traction cord 74 may also travel around or otherwise be coupled to post 26, or traction cord 74 may travel around or otherwise be coupled to hollow shaft 86.

In one specific example, anchor loop 98 may be secured to anchor pin 99, and traction cord 74 may follow a cord path that travels from anchor pin 99, toward proximal end region 17 of traction splint 10, around a portion of first adjustment mechanism 24 (e.g., around post 26), and then back around anchor pin 99. Traction cord 74 may then continue proximally towards proximal end region 17, where a portion of traction cord 74 (e.g., external portion 81) may be positioned external to inner member 12. In this example, as inner member 12 is moved with respect to middle member 14 and/or outer member 16, anchor pin 99 and post 26 also are moved with respect to one another, thereby increasing the length of internal portion 79 of traction cord 74 as anchor pin 99 and post 26 are moved away from each other (e.g., as traction splint 10 is collapsed, and distal end 39 of inner member 12 moves distally, and therefore further from proximal end 100 of middle member 14), and decreasing the length of internal portion 79 of traction cord 74 as anchor pin 99 and post 26 are moved towards each other (e.g., as traction splint 10 is extended, and distal end 39 of inner member 12 moves proximally, and therefore closer to proximal end 100 of middle member 14).

A respective adjustment mechanism 18 (e.g., first adjustment mechanism 24) may be configured to selectively allow or prevent traction mechanism 70 from being adjusted. For example, loosening nut portion 27 relative to post 26 may allow traction cord 74 to be pulled, thereby engaging pulley mechanism 72 and moving inner member 12 away from distal end 36 of outer member 16. Tightening nut portion 27 relative to post 26 may secure pulley mechanism 72, thereby locking traction cord 74 in place and retaining traction splint 10 in a configuration in which traction is applied to the patient's limb.

In use, fraction splint 10 may be stored and/or transported in the collapsed configuration. To ease or facilitate such storage and/or transportation, traction splint 10 may be configured to be lightweight and/or easily portable. When needed to apply fraction to a patient's limb, and/or otherwise stabilize the patient's limb, traction splint 10 may be extended to the desired length. Traction splint 10 may be configured to be secured to the patient's limb such that inner member 12 and outer member 16 are positioned adjacent a predetermined, desired, or selected portion of the patient's limb (e.g., on the lateral (outside) portion of the limb). In use on a lower limb, such as a patient's leg, proximal strap 30 may be configured to be positioned around the patient's thigh, adjacent the patient's pelvis, or around the patient's waist. Distal strap 34 may be configured to be positioned around the patient's upper or lower leg, such as adjacent and distal to the patient's knee. In some examples distal strap 34 may positioned adjacent the patient's shin or ankle. In other examples, fraction splint 10 may be secured to a patient's arm, such that proximal strap 30 is secured to a selected (lateral, medial, anterior, and/or posterior) portion of the patient's upper arm (proximal to the elbow), and distal strap 34 is secured to a selected portion of the patient's forearm (distal to the elbow). In some examples, such as in cases of a pelvis fracture, proximal strap 30 may be secured to the patient's pelvis (e.g., proximal loop 47 may be formed around the patient's pelvis), to assist in stabilization of the pelvis fracture and to limit internal bleeding. Other configurations are also possible, depending upon the type and location of the injury, as well as the size of the patient.

For example, while traction splints 10 are generally described herein as being secured to a patient's limb, such traction splints 10 may be secured to more than one limb in similar manners as described above. In the specific example of a patient with bilateral lower limb fractures (e.g., bilateral femur fractures), presently disclosed traction splints 10 may be secured to both of the patient's legs, with proximal strap 30 being configured to serve as an anchor point for applying traction to the bilateral limb fractures.

In addition to adjusting the length of traction splint 10, one or more respective straps 28 and/or one or more respective strap fasteners 42 may be selectively adjusted between the right-limb orientation and the left-limb orientation, for use on a patient's right limb or left limb, respectively. For example, proximal strap 30 and/or proximal strap fastener 43 may be configured to be selectively and reversibly rotated with respect to inner member 12, between a right-limb orientation and a left-limb orientation. As an example, in the right-limb orientation, proximal strap fastener 43 may be configured to be positioned adjacent an anterior portion of the patient's right limb and/or adjacent a lateral portion of the patient's right limb, and proximal strap 30 may be configured to be secured around the patient's right limb by traveling posteriorly from inner member 12, towards a medial portion of the patient's right limb, and then be secured via proximal strap fastener 43. As a corresponding example, in the left-limb orientation, proximal strap fastener 43 may be configured to be positioned adjacent an anterior portion of the patient's left limb and/or adjacent a lateral portion of the patient's left limb, and proximal strap 30 may be configured to be secured around the patient's left limb by traveling posteriorly from inner member 12 towards a medial portion of the patient's left limb, and then be secured via proximal strap fastener 43. Proximal strap fastener 43 and/or proximal strap 30 may be rotated approximately 180 degrees in selectively switching between the right-limb orientation and the left-limb orientation.

Additionally or alternatively, distal strap 34 and/or distal strap fastener 45 may be configured to be selectively and reversibly rotated with respect to outer member 16, between a right-limb orientation and a left-limb orientation. For example, in a right-limb orientation, distal strap fastener 45 of distal strap 34 may be configured to be positioned adjacent an anterior portion of the patient's right limb and/or adjacent a lateral portion of the patient's right limb, and distal strap 34 may be configured to be secured around the patient's right limb by traveling posteriorly from outer member 16 towards a medial portion of the patient's right limb, and then be secured via distal strap fastener 45. Similarly, in the left-limb orientation, distal strap fastener 45 of distal strap 34 may be configured to be positioned adjacent an anterior portion of the patient's left limb and/or adjacent a lateral portion of the patient's left limb, and distal strap 34 may be configured to be secured around the patient's left limb by traveling posteriorly from outer member 16 towards a medial portion of the patient's left limb, and then be secured via distal strap fastener 45. Distal strap fastener 45 and/or distal strap 34 may be rotated approximately 180 degrees in selectively switching between the right-limb orientation and the left-limb orientation.

Some examples of traction splints 10 may include one or more tourniquet portions 90, such as may be coupled to distal strap 34 and/or coupled to proximal strap 30. Tourniquet portion 90 may be configured to be sufficiently constricted around a portion of the patient's limb to at least partially occlude blood flow through the portion of the patient's limb. For example, tourniquet portion 90 may include a ratchet mechanism configured to tighten proximal strap 30 and/or distal strap 34 sufficiently enough such that it at least partially occludes blood flow to a portion of the patient's limb. In some examples, such as in the case of a patient with a pelvis fracture, tourniquet portion 90 (e.g., a tourniquet portion 90 coupled to proximal strap 30) may be used to help stabilize the pelvis fracture.

Inner member 12, middle member 14, and/or outer member 16 may be substantially cylindrical members having an at least substantially circular cross-sectional area in some examples. In other examples, inner member 12, middle member 14, and/or outer member 16 may have cross-sectional areas of different shapes, such as a square-shaped, rectangular, rhombus-shaped, trapezoidal, elliptical, oval, or other polygonal or non-circular cross-sectional area. Inner member 12, middle member 14, and/or outer member 16 may be substantially hollow, each being formed of a relatively thin-walled elongate structure, defining an interior space that may receive a respective other of the inner member 12, middle member 14, and/or traction mechanism 70. Inner member 12, middle member 14, and/or outer member 16 may be arranged to be at least substantially concentric with respect to one another. Inner member 12, middle member 14, and/or outer member 16 may be non-foldable members.

Inner member 12, middle member 14, and/or outer member 16 may be formed of any suitable material. Suitable materials include materials that have sufficient tensile strength to apply fraction and stability to a human limb. Suitable materials also may be sufficiently rigid to resist bending while in use (e.g., in an extended configuration), yet may be resilient enough to resist fractures, cracks, and other damage while in use or when being transported. Suitable materials also may be relatively lightweight, in order to increase ease of portability. Suitable materials include metallic materials (e.g., aluminum, titanium, etc.), metal alloys (such as steel), carbon fiber materials, polymers, and/or any other materials having suitable properties for the application.

Figure 2:
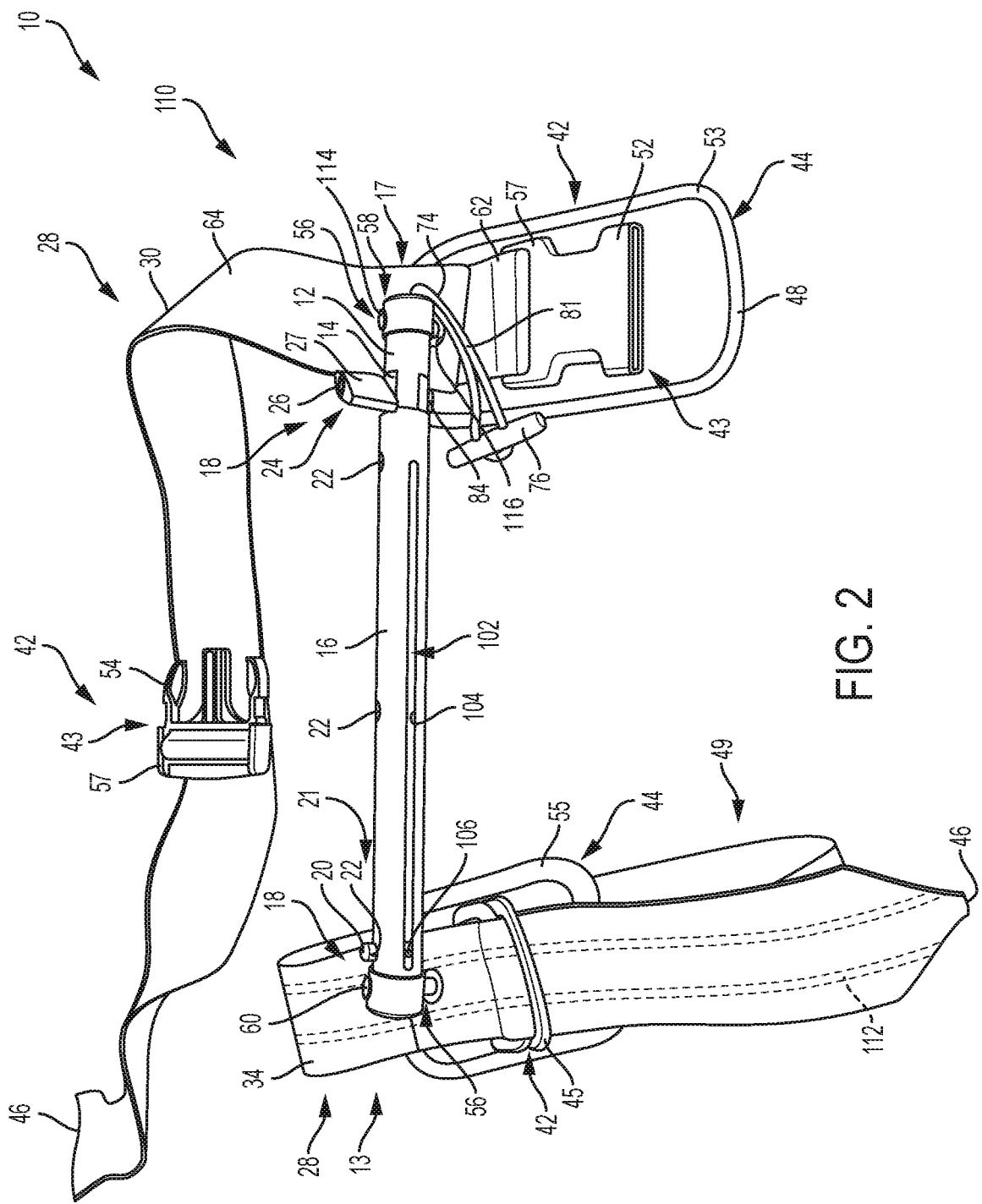
FIG. 2 is an elevation view of an example of a traction splint according to the present disclosure, the traction splint being in a collapsed configuration.
Figure 3:
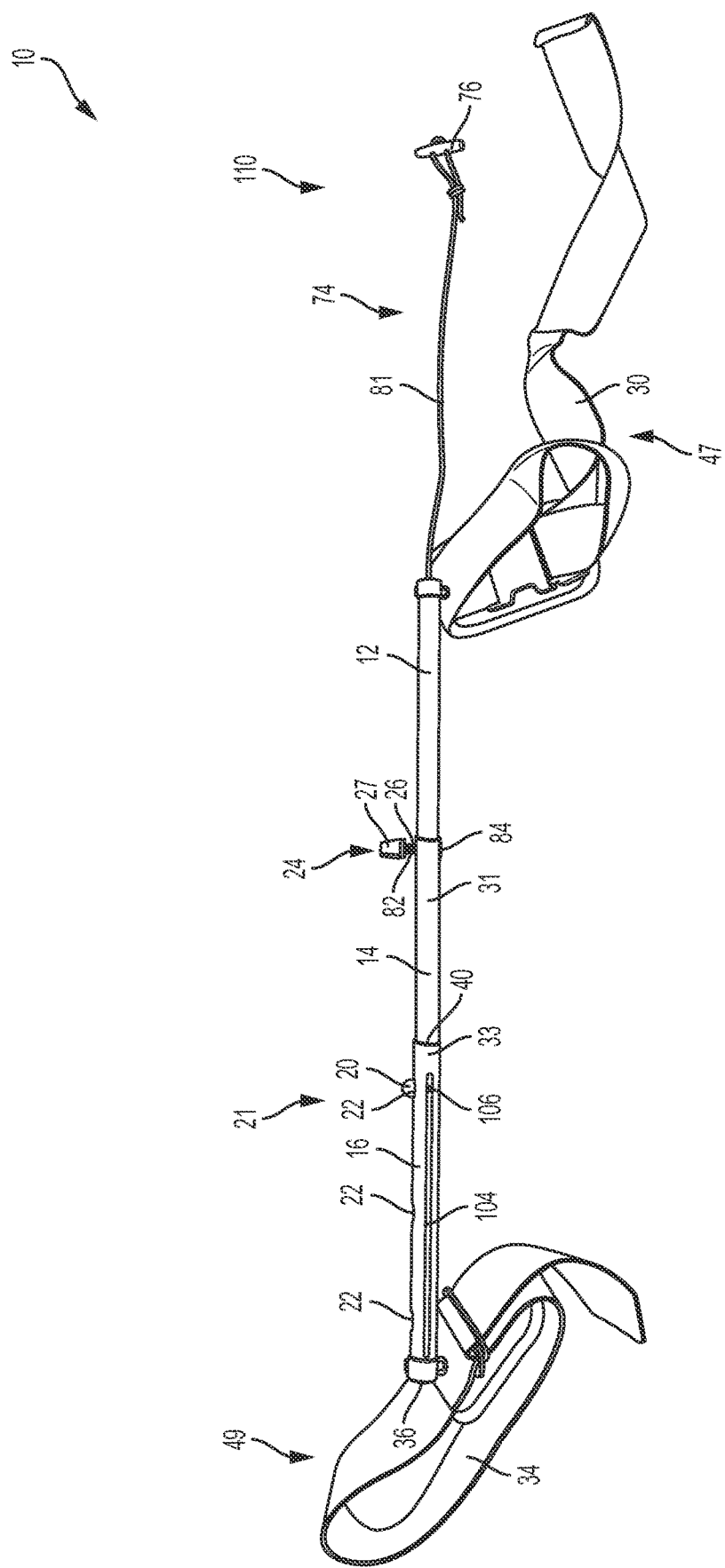
FIG. 3 is an elevation view of the traction splint of FIG. 2 in an extended configuration.
Figure 4:
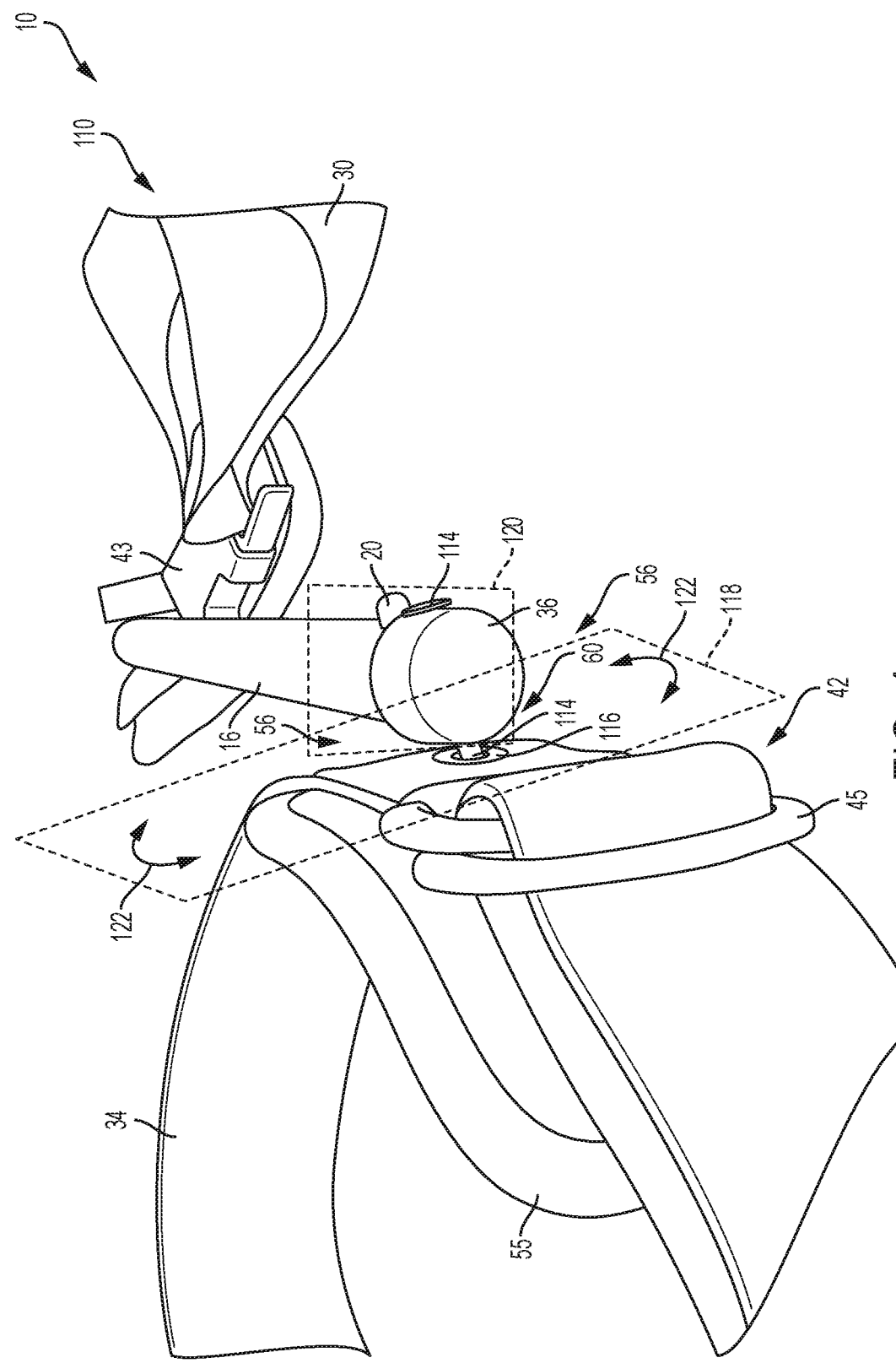
FIG. 4 is a perspective view of a portion of an example of a traction splint according to the present disclosure, showing a distal strap and a distal strap connector.
Figure 5:
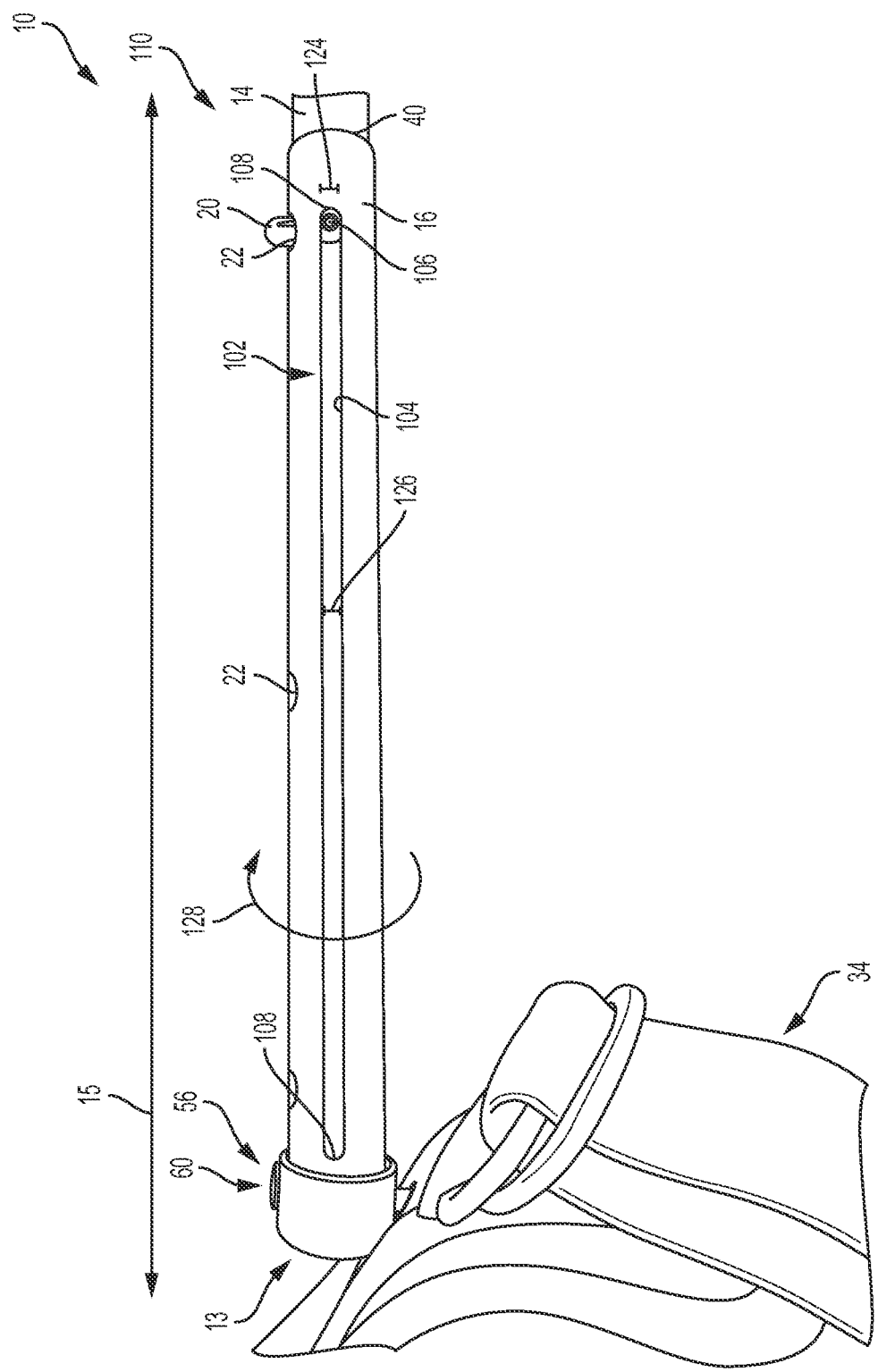
FIG. 5 is an elevation view of a portion of an example of a traction splint according to the present disclosure, showing an outer member having an anti-rotation feature.

Turning now to FIGS. 2-6, a fraction splint 110, which is an example of traction splint 10, is shown in a collapsed configuration (FIG. 2), and at least partially extended towards an extended configuration (FIG. 3). FIGS. 4-6 illustrate close-ups of various features of traction splint 110, such as distal strap connector 60 (FIG. 4), anti-rotation feature 102 (FIG. 5), and traction cord 74 (FIG. 6).

Traction splint 110 includes inner member 12, middle member 14, and outer member 16. In the collapsed configuration of FIG. 2, inner member 12 may be almost entirely positioned within middle member 14, and middle member 14 may be almost entirely positioned within outer member 16. Proximal strap 30 may be coupled to inner member 12 adjacent proximal end region 17 of traction splint 110 via proximal strap connector 58, and distal strap 34 may be coupled to outer member 16 adjacent distal end region 13 of traction splint 110 via distal strap connector 60. External portion 81 of traction cord 74 having stopper 76 coupled thereto, is shown extended from inner member 12 adjacent proximal end region 17.

Proximal strap 30 is shown with free end 46 and terminal end 48, with first fastener part 52 (e.g., a female portion of a side-squeeze buckle, as shown) of proximal strap fastener 43 coupled to proximal padding portion 53, adjacent terminal end 48 of proximal strap 30. Proximal strap fastener 43 also may include second fastener part 54 (e.g., a male portion of the side-squeeze buckle, as shown), coupled to proximal strap 30, such as via ladderlock 57. To form proximal loop 47 (FIG. 3), second fastener part 54 may be inserted into first fastener part 52.

Distal strap 34 is shown in a distal loop 49, where free end 46 of distal strap 34 has been inserted through distal strap fastener 45 (e.g., a pair of D-rings) to form distal loop 49. As shown in FIG. 2, distal strap 34 may include a rubberized portion 112, which may impart elasticity to distal strap 34 and/or may improve the grip of distal strap 34 in use around a patient's limb. For example, rubberized portion 112 may include a plurality of elastic fibers embedded within distal strap 34, but other configurations are also possible. Additionally or alternatively, proximal strap 30 may include a rubberized portion 112 as described in connection with distal strap 34.

FIG. 3 illustrates traction splint 110 of FIG. 2 that has been at least partially extended towards the extended configuration. As shown in FIG. 3, when traction splint 110 is extended, at least a portion of inner member 12 may be positioned outside of middle member 14, and at least a portion of middle member 14 may be positioned outside of outer member 16. To extend traction splint 110, first adjustment mechanism 24 may be loosened (e.g., nut portion 27 may be loosened relative to post 26) to allow inner member 12 to be longitudinally slid with respect to middle member 14. To further extend traction splint 110, second adjustment mechanism 21 may be used, such that plunger 20 may be depressed, and middle member 14 may be longitudinally slid with respect to outer member 16 until plunger 20 is positioned to extend through the desired adjustment hole 22 of second adjustment mechanism 21. For example, in the collapsed configuration of FIG. 2, plunger 20 is shown extending through the respective adjustment hole 22 adjacent distal end region 13 and distal end 36 of outer member 16. In the extended configuration of FIG. 3, plunger 20 is shown extending through a different respective adjustment hole 22 (e.g., the respective adjustment hole 22 adjacent proximal end 40 of outer member 16).

Due to longitudinal movement of middle member 14 with respect to outer member 16, pin 106 of middle member 14 is shown in a different position (e.g., more proximally located) within longitudinally-extending slot 104 in FIG. 3 as compared to FIG. 2. Additionally, as shown in FIG. 3, external portion 81 of traction cord 74 is longer in length than the external portion 81 of traction cord 74 of the configuration shown in FIG. 2, due to the longitudinal movement of inner member 12 with respect to middle member 14.

FIG. 4 shows a close-up of a portion of traction splint 110 of FIGS. 2-3, illustrating distal strap connector 60 (an example of strap connector 56), which is configured to couple distal strap 34 to outer member 16 of traction splint 110. Distal strap connector 60 may couple distal strap 34, distal strap fastener 45, and/or distal padding portion 55 to outer member 16 of traction splint 110. Proximal strap connector 58 may be similarly configured, in some examples.

Distal strap connector 60 may include at least a first fastening component 114 and a second fastening component 116. In some examples, first fastening component 114 may be substantially stationary with respect to outer member 16, and second fastening component 116 may be configured to selectively rotate about first fastening component 114, thereby selectively rotating distal strap 34, distal strap fastener 45, and/or distal padding 55 with respect to outer member 16. For example, first fastening component 114 may include one or more bolts, pins, rivets, and/or posts extending through outer member 16, distal strap 34, and/or distal padding portion 55. In examples where distal strap 34 includes a distal first strap portion 66 and a distal second strap portion 68, first fastening component 114 may extend through one or both of the portions 66, 68 (see FIG. 1). Second fastening component 116 may be, for example, one or more grommets that are sized and shaped to rotate freely about first fastening component 114. For example, distal strap 34 and/or distal padding portion 55 may include respective second fastening components 116, through which first fastening component 114 may be inserted.

Distal strap connector 60 may thus be configured such that the entire distal strap 34 and/or distal strap fastener 45 may be rotated with respect to outer member 16, between a left-limb orientation and a right-limb orientation. In some examples, such rotation of distal strap 34 and/or distal strap fastener 45 may be in a plane of rotation 118 that is at least substantially perpendicular to a cross-sectional plane 120 defined by the cross-sectional area of outer member 16. Arrow 122 indicates the general directions of movement in plane of rotation 118. In some examples, distal strap 34 may be freely rotatable such that second fastening component 116 may freely spin around first fastening component 114 continuously, any number of times. In other examples, the range of motion may be limited, such that, for example, distal strap 34 may be rotatable in one direction to a certain extent (e.g., may be rotatable at least about 180 degrees in one direction), and then may be prevented from rotating further in that direction, requiring rotation in the opposite direction to further move distal strap 34.

Proximal strap connector 58 (FIGS. 2-3) may be configured similarly. For example, a respective first fastening component 114 and second fastening component 116 may be arranged such that first fastening component 114 is substantially stationary with respect to inner member 12 and such that second fastening component 116 may rotate freely about first fastening component 114. In this manner, proximal strap 30 may be configured to rotate with respect to inner member 12 in a similar manner as described in connection with distal strap 34 in FIG. 4. In some examples, both proximal strap 30 and distal strap 34 may be configured to rotate between such right-limb and left-limb configurations. In other examples, just one of proximal strap 30 and distal strap 34 may be configured to so rotate.

FIG. 5 illustrates a close-up of anti-rotation feature 102, which may be configured to prevent rotation of middle member 14 with respect to outer member 16, both while stationary and while traction splint 110 is being extended towards the extended configuration. As shown in FIG. 5, anti-rotation feature 102 may include a longitudinally-extending slot 104 formed in outer member 16. A pin 106 coupled to middle member 14 may extend at least partially through longitudinally-extending slot 104 such that longitudinal movement of middle member 14 with respect to outer member 16 results in longitudinal movement of pin 106 within longitudinally-extending slot 104.

A diameter 124 of pin 106 may be slightly less than a width 126 of longitudinally-extending slot 104. In this manner, pin 106 may be configured to be substantially prevented from moving with respect to longitudinally-extending slot 104 in any direction other in the longitudinal directions indicated by arrow 15. Thus, anti-rotation feature 102 may be configured to substantially prevent rotation of middle member 14 with respect to outer member 16 (e.g., rotation in the circumferential direction, as indicated by arrow 128). Ends 108 of longitudinally-extending slot 104 may limit the extent to which middle member 14 may be longitudinally moved with respect to outer member 16. For example, middle member 14 may be limited in the amount it may be inserted into outer member 16 by pin 106 colliding with the end 108 of longitudinally-extending slot 104 adjacent distal end region 13 of traction splint 110. Similarly, middle member 14 may be limited in the amount it may be extended out from outer member 16 by pin 106 colliding with the end 108 of longitudinally-extending slot 104 adjacent proximal end 40 of outer member 16. In this manner, anti-rotation feature 102 may be configured to prevent separation of middle member 14 from outer member 16.

FIG. 6 illustrates a portion of traction splint 110, with inner member 12 extended with respect to middle member 14 and outer member 16. With respect to FIGS. 2-3, traction splint 110 has been rotated approximately ninety degrees in FIG. 6, which shows fraction splint 110 from the top. In this view, an inner member slot 88 is visible being formed through inner member 12. Inner member slot 88 maybe sized and shaped such that inner member slot 88 passes on either side of post 26 of first adjustment mechanism 24 as inner member 12 is moved longitudinally with respect to middle member 14.

Figure 7:
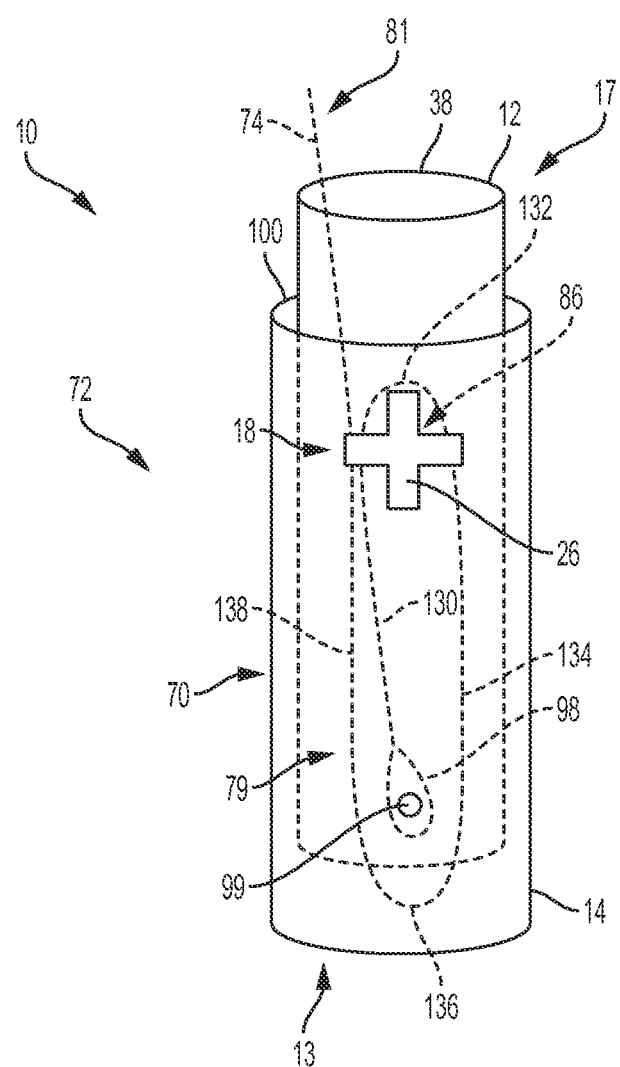
FIG. 7 is a schematic representation of examples of a cord path for a traction cord of a traction splint according to the present disclosure, viewed from the top.
Figure 8:
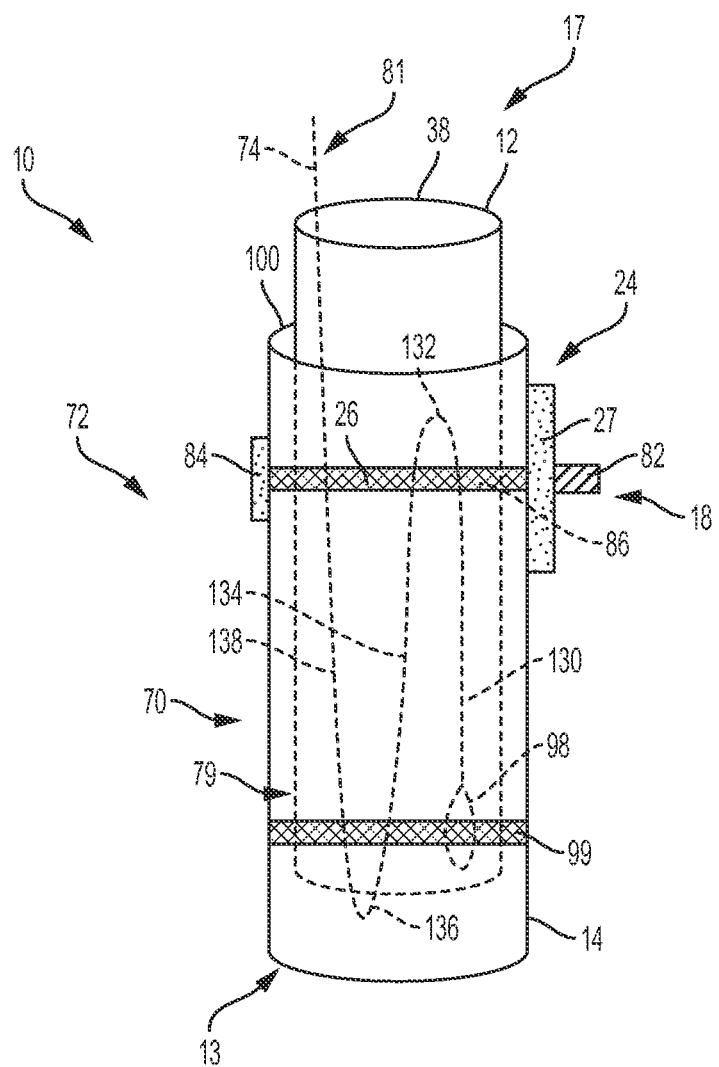
FIG. 8 is a schematic partial cross-sectional representation of examples of a cord path for a traction cord of a traction splint according to the present disclosure, viewed from the side.

As shown in FIG. 6, external portion 81 of fraction cord 74 extends out from inner member 12 adjacent proximal end region 17 of traction splint 110. The cord path of traction cord 74 creates pulley mechanism 72 using post 26 of first adjustment mechanism 24 and anchor pin 99 positioned within inner member 12. For example, as shown schematically in FIGS. 7-8, internal portion 79 of traction cord 74 may include an anchor loop 98 coupled to anchor pin 99, from which traction cord 74 may travel proximally (e.g., towards proximal end region 17 of traction splint 110) for a first cord path segment 130 of traction cord 74. Traction cord 74 may extend around post 26 of first adjustment mechanism 24, such as indicated at 132. Traction cord 74 may then travel distally (e.g., towards distal end region 13 of traction splint 110) along a second cord path segment 134 and travel around anchor pin 99, as indicated at 136. Finally, traction cord 74 may again travel proximally along a third cord path segment 138, to exit inner member 12 adjacent proximal end region 17 of traction splint 110. The respective lengths of the cord path segments may vary depending on the distance between anchor pin 99 and post 26, which in turn depends on the extent to which inner member 12 is extended with respect to middle member 14. Only inner member 12 and middle member 14 of traction splint 10 are shown in FIGS. 7-8, for clarity, with inner member 12 being positioned partially nested inside middle member 14.

In operation, as a user applies a tension force to external portion 81 of traction cord 74 (e.g., as a user pulls on stopper 76, in a direction proximally away from inner member 12), traction cord 74 urges anchor pin 99 of inner member 12 toward post 26, thereby extending inner member 12 out from within middle member 14, and applying traction when traction splint 10 is in place on a patient's limb. In this manner, pulley mechanism 72 may have a traction cord 74 that follows a cord path that utilizes the same feature as an adjustment mechanism 18 (e.g., post 26 and/or hollow shaft 86 for first adjustment mechanism 24). Such a cord path may reduce manufacturing time and/or costs by reducing the number of parts in traction mechanism 70.

Figure 9:
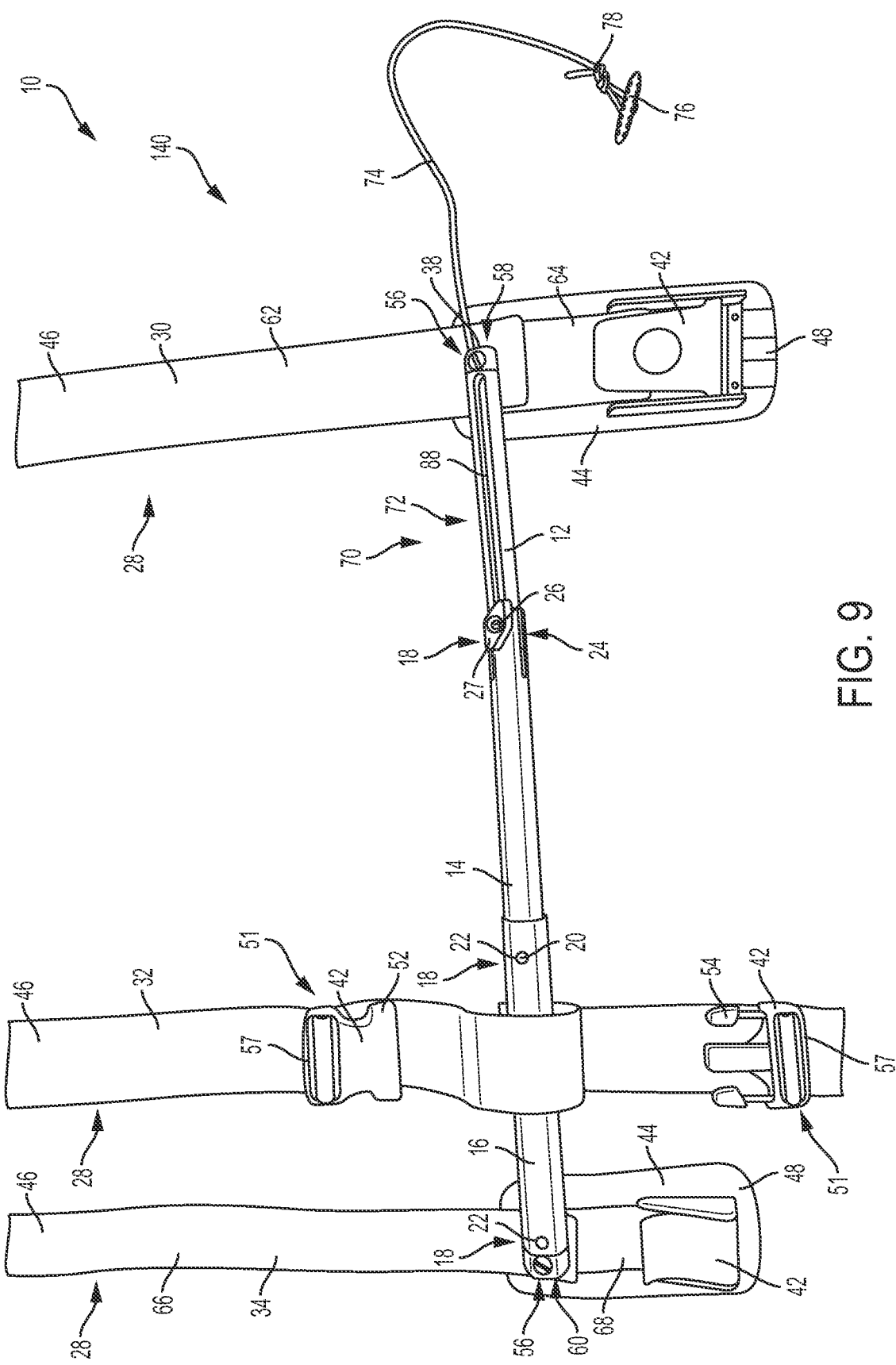
FIG. 9 is a top plan view of an example of a traction splint according to the present disclosure, the traction splint being in an extended configuration, the proximal strap and distal strap being in a right-limb orientation.
Figure 10:
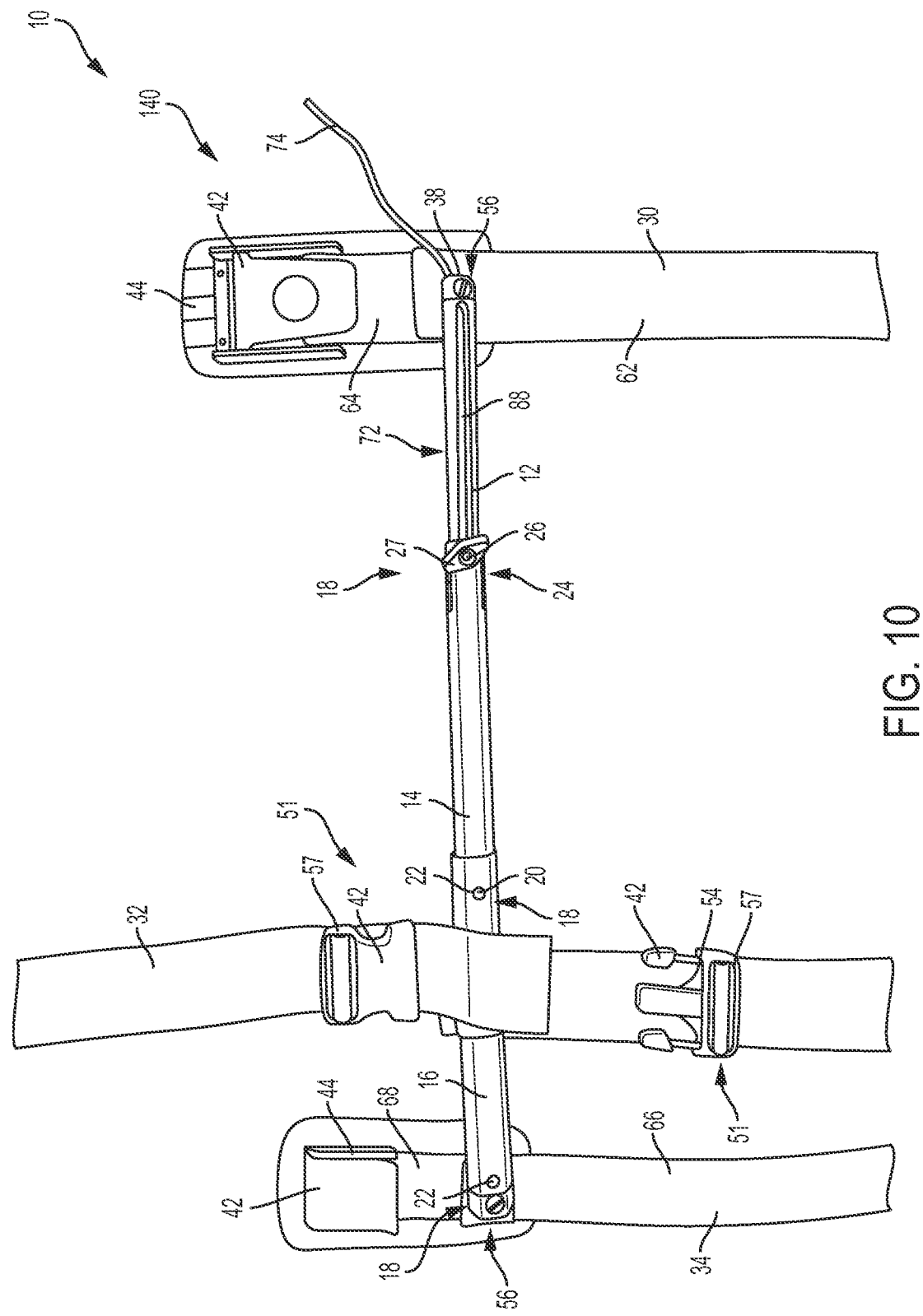
FIG. 10 is a top plan view of the traction splint of FIG. 7, with the proximal strap and the distal strap being in a left-limb orientation.

FIGS. 9-10 illustrate a traction splint 140, which is another example of traction splint 10 according to the present disclosure. A proximal strap 30 and a distal strap 34 of traction splint 140 may include a respective strap fastener 42, such as a cam or lever buckle, and a respective padding portion 44 configured to increase comfort for a patient. Strap fasteners 42 may be positioned adjacent a respective terminal end 48 of each of proximal strap 30 and distal strap 34. A respective free end 46 of proximal strap 30 and of distal strap 34 may be inserted through a respective fastener 42 and secured such that the straps are taut around a patient's limb.

Proximal strap 30 may be formed by a proximal first strap portion 62 and a proximal second strap portion 64, and distal strap 34 may be formed by a distal first strap portion 66 and a distal second strap portion 68. Proximal first strap portion 62 and proximal second strap portion 64 may each be coupled to a respective strap connector 56 (e.g., a proximal strap connector 58), which may be configured to allow articulation or rotation of proximal first strap portion 62 and proximal second strap portion 64 with respect to an inner member 12. Similarly, distal first strap portion 66 and distal second strap portion 68 may each be coupled to a respective strap connector 56 (e.g., a distal strap connector 60), which may be configured to allow articulation or rotation of distal first strap portion 66 and distal second strap portion 68 with respect to an outer member 16. Traction splint 140 may include a traction mechanism 70 having a pulley mechanism 72 at least partially contained within inner member 12. Pulley mechanism 72 may include a traction cord 74, which may at least partially extend out from a proximal end 38 of inner member 12. Traction cord 74 may include a stopper 76 to assist in pulling traction cord 74 and/or to prevent traction cord 74 from being drawn entirely within inner member 12.

FIGS. 9 and 10 show traction splint 140 in an extended configuration, with inner member 12 at least partially extended out from a middle member 14, and with middle member 14 at least partially extended out from outer member 16. In order to extend traction splint 140 towards the extended configuration shown in FIG. 3, adjustment mechanisms 18 may be used. For example, a plunger 20 may be pressed radially inward to allow middle member 14 to slide out from within outer member 16, with the spring bias forcing plunger 20 through an adjustment hole 22 formed in outer member 16, thereby preventing further movement of middle member 14 with respect to outer member 16.

As compared to FIG. 9, FIG. 10 shows proximal strap 30 and distal strap 34 in a different orientation, demonstrating the articulating, or rotating, function of straps 28 and strap connectors 56. Inner member 12, middle member 14, outer member 16, and traction cord 74 are in similar configurations in both FIG. 9 and FIG. 10, for reference; however, proximal strap 30 and distal strap 34 have each been rotated approximately 180 degrees with respect to inner member 12 and outer member 16 (which are substantially aligned with each other), respectively. FIG. 9 illustrates traction splint 140 in a right-limb orientation (e.g., configured to be secured to a patient's right limb with the members (12, 14, 16) positioned against or adjacent the lateral (outside) portion of the patient's right limb), and FIG. 10 illustrates traction splint 140 in a left-limb orientation (e.g., configured to be secured to a patient's left limb with the members (12, 14, 16) positioned against or adjacent the lateral (outside) portion of the patient's left limb).

In FIGS. 9 and 10, proximal strap 30 may comprise proximal first strap portion 62 and proximal second strap portion 64. As shown in FIG. 9, proximal first strap portion 62 is oriented toward the top of the figure, while in FIG. 10, proximal first strap portion 62 is oriented toward the bottom of the figure, thus being rotated approximately 180 degrees. Further, proximal second strap portion 64 is oriented toward the bottom of FIG. 9, and is rotated approximately 180 degrees to be oriented toward the top of FIG. 10. Similarly, as shown in FIG. 9, distal first strap portion 66 is oriented toward the top of the figure, while in FIG. 10, distal first strap portion 66 is oriented toward the bottom of the figure, thus being rotated approximately 180 degrees. Further, distal second strap portion 68 is oriented toward the bottom of FIG. 9, and is rotated approximately 180 degrees to be oriented toward the top of FIG. 10. Rotating the straps 180 degrees is used for illustration purposes, but strap connectors 56 may be configured such that the straps or portions thereof may be selectively rotated or articulated any number of degrees with respect to the members of traction splint 140.

Figure 11:
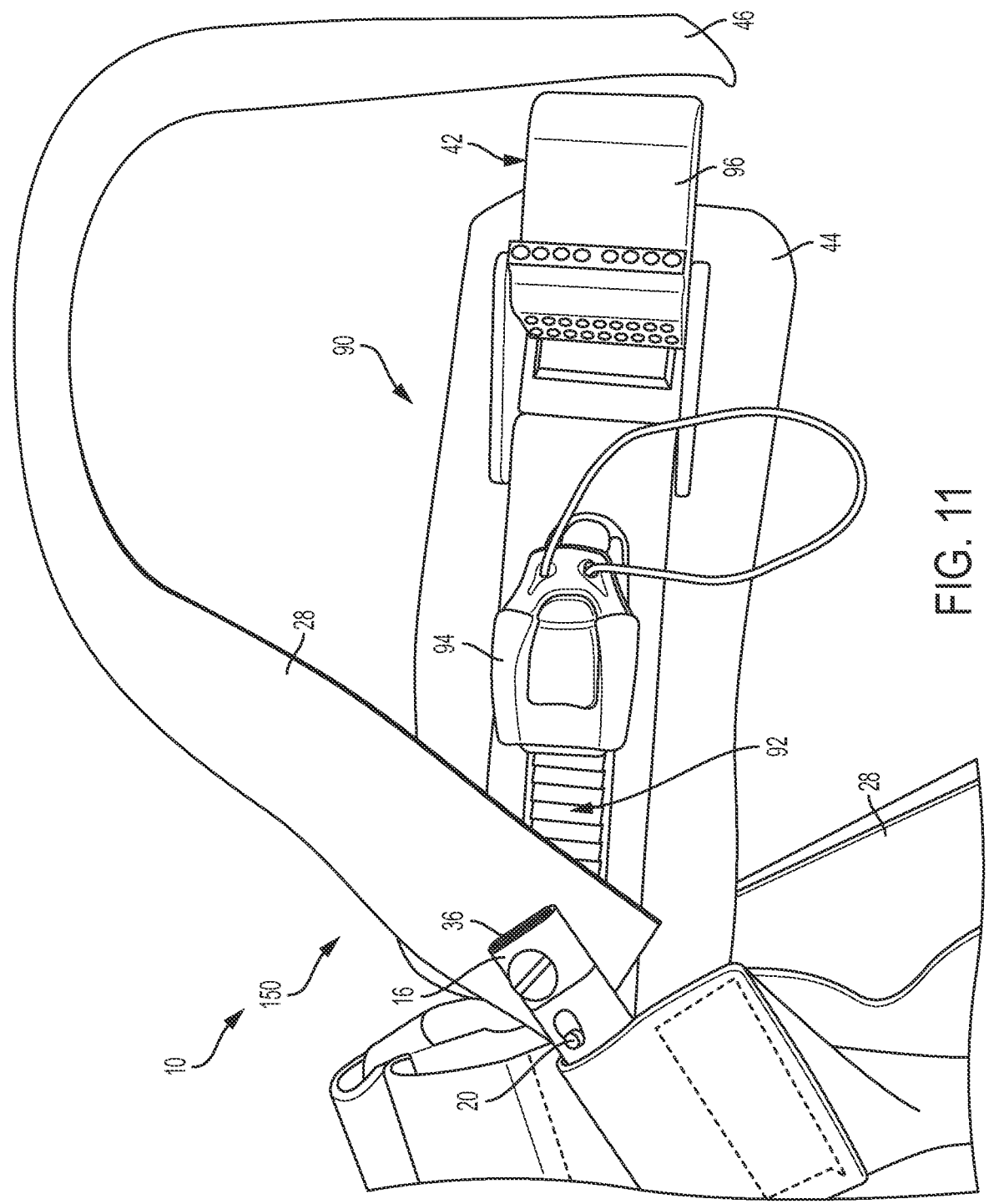
FIG. 11 is a top plan view of a portion of an example of a traction splint according to the present disclosure, showing a tourniquet portion that may be included on the fraction splint.

FIG. 11 shows a portion of a fraction splint 150, which is another example of traction splint 10 according to the present disclosure. Traction splint 150 includes a strap 28 with a strap fastener 42 that is configured to function as a tourniquet portion 90 (e.g., strap 28 of tourniquet portion 90 may be configured to be sufficiently constricted around a portion of a patient's limb via strap fastener 42, so as to at least partially occlude blood flow to the portion of the patient's limb). Tourniquet portion 90 is shown as being coupled to traction splint 150 adjacent a distal end 36 of an outer member 16 of traction splint 150, however tourniquet portion 90 may be included in different portions of traction splint 150 (e.g., a tourniquet portion 90 may be included that is coupled to a proximal strap 30, adjacent a proximal end 38 of an inner member 12). Tourniquet portion 90 may include a ratcheting mechanism 92 to tighten the tourniquet portion and a release lever 94 to release, or loosen, tourniquet portion 90. In use, a free end 46 of strap 28 (e.g., a distal strap 34) may be inserted through strap fastener 42, which may be a lever or cam buckle 96, and the lever or cam buckle 96 may be closed, thereby initially securing strap 28 in place around a patient's limb. Strap 28 then may be cinched further around the patient's limb using ratcheting mechanism 92 of tourniquet portion 90 until strap 28 is tight enough to at least partially (sufficiently) occlude (e.g., stop) or reduce the flow of blood past the site of the tourniquet portion. While FIG. 11 shows ratcheting mechanism 92, other mechanisms also are within the scope of the present disclosure, however, the term "tourniquet" is used to mean an occluding action that is stronger and more effective than possibly attained using simply a strap and buckle. Tourniquet 90 may be utilized with or in place of any of the strap fasteners of any of the examples of traction splints 10 disclosed herein.

Figure 12:
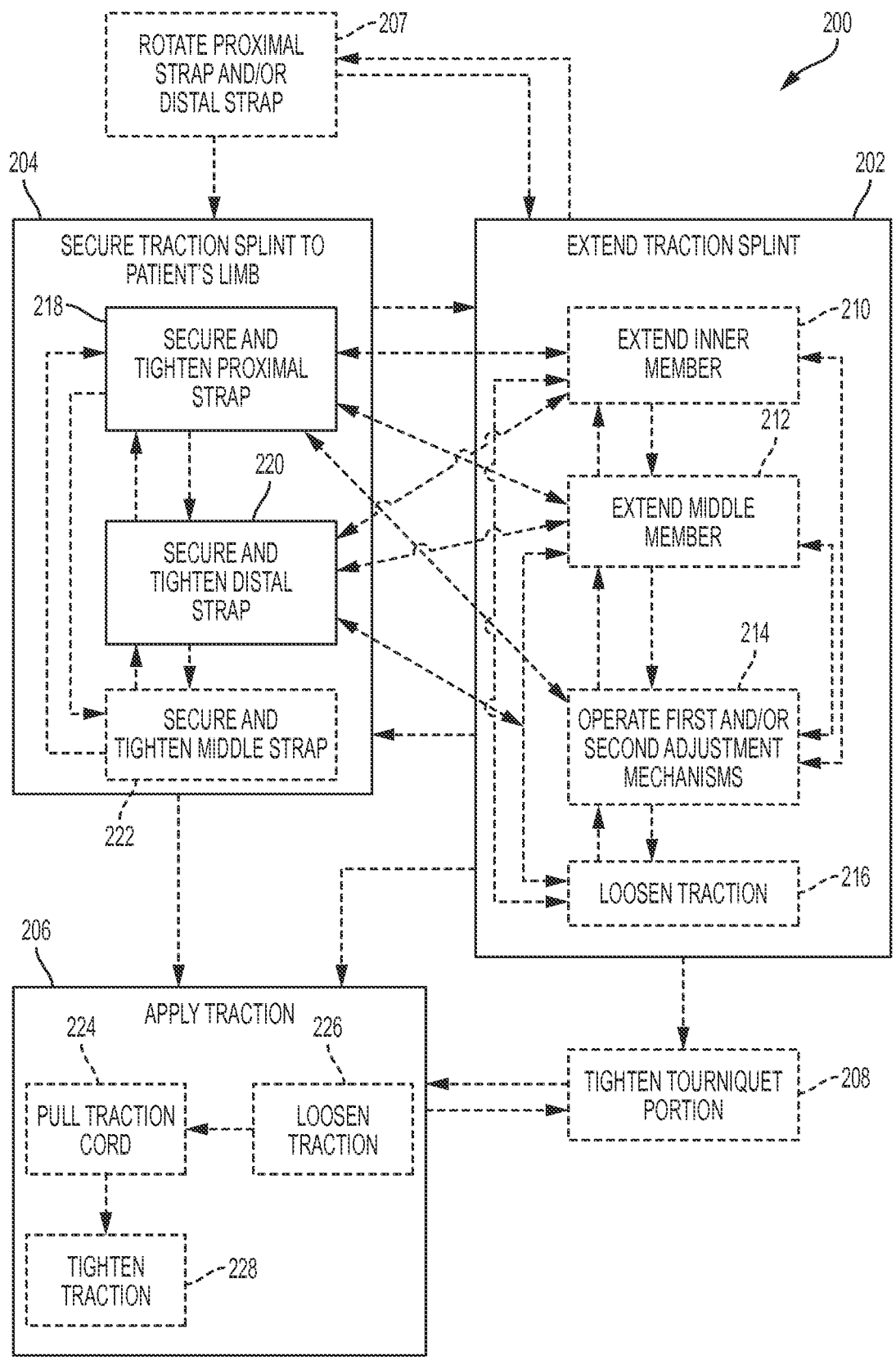
FIG. 12 is a schematic block diagram representing examples of methods of using a traction splint according to the present disclosure.

FIG. 12 shows a schematic flow chart representation of methods 200 of using presently disclosed traction splints (e.g., traction splint 10). Methods 200 generally may include extending the traction splint to an appropriate size at 202, securing the traction splint to a patient's limb at 204, and applying traction at 206. Some methods 200 additionally may include rotating a proximal strap (e.g., proximal strap 30) and/or a distal strap (e.g., distal strap 34) to either a right-limb orientation or a left-limb orientation at 207, and/or tightening a tourniquet portion (e.g., tourniquet portion 90) at 208 to at least partially occlude blood flow to a portion of the patient's limb.

Extending the traction splint at 202 may include extending an inner member (e.g., inner member 12) with respect to a middle member (e.g., middle member 14) and/or with respect to an outer member (e.g., outer member 16) at 210 and/or extending the middle member with respect to the outer member at 212. For example, a first and/or second adjustment mechanism (e.g., first adjustment mechanism 24 and/or second adjustment mechanism 21) may be engaged or operated at 214 in order to extend the inner member at 210 and/or extend the middle member at 212. In some methods, operating the first and/or second adjustment mechanisms at 214 may include depressing a plunger (e.g., plunger 20) through a respective adjustment hole (e.g., adjustment hole 22) formed in the outer member, and moving the middle member with respect to the outer member until the plunger is positioned such that it extends through a different respective adjustment hole of the outer member.

Extending the inner member at 210 may include longitudinally sliding the inner member with respect to the middle member and/or the outer member. Similarly, extending the middle member at 212 may include longitudinally sliding the middle member with respect to the outer member. Extending the inner member at 210 and extending the middle member at 212 each may include extending the respective elongate member substantially without rotating the members with respect to one another. For example, the traction splint may include an anti-rotation feature (e.g., anti-rotation feature 102) that is configured to prevent rotation of the middle member with respect to the outer member. Additionally or alternatively, extending the inner member at 210 and extending the middle member at 212 may each include extending the respective elongate member without unfolding a plurality of foldable members.

In some methods 200, extending the traction splint at 202 may include loosening traction of the traction splint at 216, such as by loosening a nut portion (e.g., nut portion 27) relative to a post (e.g., post 26, such as relative to threaded portion 82 of post 26) to enable movement of the inner member with respect to the middle member. In this manner, the traction splint may be selectively and reversibly longitudinally extended from a collapsed configuration towards an extended configuration, to an extent such that the traction splint is sized appropriately for the given size of the patient's limb. Extending the traction splint at 202 may include at least temporarily retaining the traction splint in the respective extended position between the collapsed configuration and the extended configuration, inclusive. Extending the traction splint at 202 may include increasing a distance between a proximal end region (e.g., proximal end region 17) of the traction splint and a distal end region (e.g., distal end region 13) of the traction splint.

Securing the traction splint to the patient's limb at 202 may include securing and tightening the proximal strap at 218, securing and tightening the distal strap at 220, and/or securing and tightening the middle strap (e.g., middle strap 32) at 222. For example, securing and tightening the proximal strap at 218 may include looping the proximal strap around the patient's limb (e.g., forming a proximal loop 47), fastening the proximal strap via a proximal strap fastener (e.g., proximal strap fastener 43), and tightening the proximal strap around the patient's limb, thereby securing the inner member of the traction splint to the patient's limb. Similarly, securing and tightening the distal strap at 220 may include looping the distal strap around the patient's limb (e.g., forming a distal loop 49), fastening the distal strap via a distal strap fastener (e.g., distal strap fastener 45), and tightening the distal strap around the patient's limb, thereby securing the outer member of the traction splint to the patient's limb. The traction splint may be secured to a patient's arm or leg. In methods where the traction splint is used to stabilize an upper leg injury, securing the proximal strap at 218 may include positioning the proximal strap around the patient's thigh, adjacent the patient's pelvis. In some such methods, securing the distal strap at 220 may include positioning the distal strap around the patient's lower leg, adjacent and distal to the patient's knee or ankle. Other positions also are possible.

Applying traction to the patient's limb at 206 may include pulling (e.g., applying a tension force to) a traction cord (e.g., external portion 81 of traction cord 74) at 224, thereby pressing the inner member and the outer member away from one another. In some methods 200, applying traction at 206 may include loosening traction at 226 (e.g., loosening a nut portion of a first adjustment mechanism) before pulling the traction cord, and/or tightening traction at 228 (e.g., tightening the nut portion as the traction cord is held taut), thereby locking the fraction cord in place so that the traction splint is selectively retained in an extended position in which it is applying fraction to the limb to which it is secured.

In some methods 200, before and/or after extending the traction splint at 202, the method may include rotating the proximal strap and/or the distal strap at 207 so that the fraction splint is selectively placed in a right-limb orientation or a left-limb orientation, depending on whether the traction splint is to be used to stabilize a patient's right or left limb. For example, the proximal strap and the distal strap may be rotated at 207 from the right-limb orientation to the left-limb orientation, or vice versa in order to prepare the traction splint for use. Rotating the proximal strap and/or the distal strap at 207 may include rotation in a plane (e.g., plane of rotation 118), the plane of rotation being at least substantially perpendicular to a cross-sectional plane (e.g., cross-sectional plane 120) defined by the cross-sectional area of the inner member and the outer member. In switching between the right-limb orientation and the left-limb orientation, rotating the proximal strap and/or the distal strap at 207 may include rotating the proximal strap and/or the distal strap by approximately 180 degrees. In some methods 200, the rotating the proximal strap and/or the distal strap at 207 may include rotating the entire proximal strap, rotating the proximal strap fastener, rotating the entire distal strap, and/or rotating the distal strap fastener. Rotating at 207 may include rotating the proximal strap and/or the distal strap such that the members (12, 14, 16) of the traction splint are positioned against a selected portion (e.g., lateral) of the patient's limb when the fraction splint is secured to the patient's limb. In one specific example, the proximal strap fastener may be rotated such that a female buckle portion of the proximal strap fastener is positioned on a patient's anterior thigh.

After use on a patient, the traction splint may be collapsed to or towards the collapsed configuration, and stored and/or transported until the next use. Collapsing the traction splint may decrease a distance between the proximal end region of the traction splint and the distal end region of the traction splint. Collapsing the traction splint may increase portability of the traction splint, facilitate placement in a storage bag or carrying case, and advantageously take up less space, in some examples.

In the present disclosure, several of the illustrative, non-exclusive examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently. It is also within the scope of the present disclosure that the blocks, or steps, may be implemented as logic, which also may be described as implementing the blocks, or steps, as logics. In some applications, the blocks, or steps, may represent expressions and/or actions to be performed by functionally equivalent circuits or other logic devices. The illustrated blocks may, but are not required to, represent executable instructions that cause a computer, processor, and/or other logic device to respond, to perform an action, to change states, to generate an output or display, and/or to make decisions.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of inventive subject matter according to the present disclosure are described in the following enumerated paragraphs:

A1. A traction splint configured to apply fraction to a patient's limb, the traction splint comprising:

an outer member having a distal strap coupled thereto, the distal strap being configured to secure the traction splint to the patient's limb adjacent a distal end region of the traction splint; and an inner member nested at least partially within the outer member and having a proximal strap coupled thereto, the proximal strap being configured to secure the traction splint to the patient's limb adjacent a proximal end region of the traction splint;

wherein the traction splint is configured to be selectively and reversibly extended from a collapsed configuration towards an extended configuration by sliding the inner member in a longitudinal direction with respect to the outer member.

A1.1. The traction splint of paragraph A1, wherein the traction splint is configured to be at least temporarily retained in a configuration between the collapsed configuration and the extended configuration, inclusive.

A2. The traction splint of paragraph A1 or A1.1, further comprising a first adjustment mechanism configured to selectively allow movement of the inner member with respect to the outer member.

A2.1. The traction splint of paragraph A2, wherein the first adjustment mechanism comprises a post extending through the inner member.

A2.2. The traction splint of paragraph A2 or A2.1, wherein the first adjustment mechanism comprises a threaded portion adjacent an outer surface of the inner member.

A2.3. The traction splint of any of paragraphs A2-A2.2, wherein the first adjustment mechanism comprises a nut portion positioned adjacent an/the outer surface of the inner member, wherein a/the post of the first adjustment mechanism comprises a head portion positioned adjacent the outer surface of the inner member, wherein the first adjustment mechanism is configured such that tightening the nut portion relative to a/the threaded portion of the inner member is configured to prevent movement of the inner member with respect to the outer member.

A3. The traction splint of any of paragraphs A1-A2.3, further comprising a middle member nested at least partially within the outer member, at least a portion of the middle member being positioned between the inner member and the outer member.

A4. The traction splint of paragraph A3, further comprising a second adjustment mechanism configured to selectively allow movement of the middle member with respect to the outer member.

A4.1. The traction splint of paragraph A4, wherein the second adjustment mechanism comprises a plunger, wherein the outer member comprises a plurality of adjustment holes, and wherein the plunger is spring-biased to extend through a respective one of the plurality of adjustment holes when the plunger is not depressed.

A4.2. The traction splint of paragraph A4.1, wherein the traction splint is configured to be extended towards the extended configuration by depressing the plunger and sliding the middle member longitudinally with respect to the outer member until the middle member is positioned such that the plunger extends through a desired respective adjustment hole of the outer member.

A4.3. The traction splint of paragraph A4.2, wherein the plunger is configured to prevent further longitudinal sliding of the middle member with respect to the outer member until the plunger is depressed.

A4.4. The traction splint of any of paragraphs A4-A4.3, wherein the second adjustment mechanism is configured to retain a respective position of the middle member relative to the outer member such that the middle member is not subject to loosening with respect to the outer member.

A4.5. The traction splint of any of paragraphs A4-A4.4, wherein the second adjustment mechanism does not rely on friction to retain the middle member in a/the respective position relative to the outer member.

A4.6. The traction splint of any of paragraphs A4-A4.5, wherein the second adjustment mechanism is configured to allow at least substantially longitudinal movement of the middle member with respect to the outer member.

A5. The traction splint of any of paragraphs A3-A4.6, wherein a/the first adjustment mechanism is configured to selectively allow movement of the inner member with respect to the middle member.

A5.1. The traction splint of paragraph A5, wherein the first adjustment mechanism comprises a/the post, wherein the post extends through the middle member.

A5.2. The traction splint of paragraph A5 or A5.1, wherein the first adjustment mechanism comprises a/the threaded portion adjacent an outer surface of the middle member.

A5.3. The traction splint of any of paragraphs A5-A5.2, wherein the first adjustment mechanism comprises a/the nut portion positioned adjacent an/the outer surface of the middle member, wherein a/the post of the first adjustment mechanism extends through the inner member and the middle member, and wherein the post comprises a/the head portion positioned adjacent the outer surface of the middle member.

A5.4. The traction splint of paragraph A5.3, wherein the first adjustment mechanism is configured such that tightening the nut portion relative to a/the threaded portion of the inner member is configured to prevent movement of the inner member with respect to the middle member.

A5.5. The traction splint of paragraph A5.3, wherein the first adjustment mechanism is configured such that tightening the nut portion relative to a/the threaded portion locks a traction cord, such that the traction splint sustains a fraction force on the patient's limb.

A5.6. The traction splint of any of paragraphs A5-A5.5, wherein a/the post of the first adjustment mechanism extends through the middle member and forms a/the threaded portion adjacent an/the outer surface of the middle member.

A5.7. The traction splint of any of paragraphs A5-A5.6, wherein a/the post of the first adjustment mechanism extends through the middle member, and wherein the post is threaded.

A5.8. The traction splint of any of paragraphs A5-A5.7, wherein the first adjustment mechanism is configured to allow at least substantially longitudinal movement of the inner member with respect to the middle member.

A6. The traction splint of any of paragraphs A3-A5.8, wherein the middle member is configured to be selectively slid in the longitudinal direction with respect to the outer member.

A7. The traction splint of any of paragraphs A3-A6, wherein the inner member is configured to be selectively slid in the longitudinal direction with respect to the middle member.

A8. The traction splint of any of paragraphs A3-A7, wherein the traction splint is configured to extend from the collapsed configuration towards the extended configuration by sliding the middle member in the longitudinal direction with respect to the outer member, and by sliding the inner member in the longitudinal direction with respect to the middle member.

A9. The traction splint of any of paragraphs A1-A8, further comprising a traction mechanism having a/the traction cord, wherein the traction mechanism is configured to apply traction such that the inner member and the outer member are pressed away from one another when the traction cord is pulled.

A9.1. The fraction splint of paragraph A9, wherein an external portion of the traction cord extends from the inner member adjacent the proximal end region of the traction splint, wherein the traction mechanism is configured to apply traction such that the inner member and the outer member are pressed away from one another when a tension force is applied to the external portion of the traction cord.

A9.2. The fraction splint of paragraph A9 or A9.1, wherein the traction mechanism comprises a pulley.

A10. The traction splint of paragraph A9.1 or A9.2, wherein the traction cord comprises a stopper coupled to the external portion, the stopper being configured to limit the extent to which the traction cord may be drawn into the inner member as the traction splint is extended towards the extended configuration.

A10.1. The traction splint of paragraph A10, wherein the stopper is configured to provide a handle for a user, wherein pulling the stopper away from the inner member causes the traction splint to apply traction when secured to a patient's limb.

A11. The traction splint of any of paragraphs A9-A10.1, wherein an internal portion of the fraction cord is positioned at least partially within the inner member.

A12. The traction splint of paragraph A11, wherein the internal portion of the traction cord is positioned at least partially within the middle member.

A13. The fraction splint of any of paragraphs A9-A12, wherein the traction cord follows a cord path that travels around at least a portion of a/the first adjustment mechanism.

A13.1. The traction splint of any of paragraphs A9-A13, wherein the traction cord is coupled to a/the first adjustment mechanism configured to selectively allow movement of the inner member with respect to a/the middle member.

A13.2. The traction splint of any of paragraphs A9-A13.1, wherein the traction cord is coupled to a/the first adjustment mechanism configured to selectively allow movement of the inner member with respect to the outer member.

A13.3. The traction splint of any of paragraphs A9-A13.2, wherein the traction cord comprises an anchor loop that is anchored around an anchor pin positioned within the inner member.

A13.4. The traction splint of any of paragraphs A9-A13.3, wherein the traction cord follows a/the cord path that travels from a/the anchor pin, toward the proximal end region of the traction splint, around a portion of a/the first adjustment mechanism configured to selectively allow movement of the inner member with respect to a/the middle member, and then back around the anchor pin.

A13.5. The traction splint of paragraph A13.4, wherein the portion of the first adjustment mechanism comprises a/the post extending through the inner member.

A13.6. The traction splint of paragraph A13.4 or A.13.5, wherein the portion of the first adjustment mechanism comprises a/the post, wherein the post extends through a/the middle member.

A14. The fraction splint of any of paragraphs A1-A13.6, wherein the traction splint is configured to apply traction to the patient's limb via a/the traction mechanism adjacent the proximal end region of the traction splint.

A15. The traction splint of any of paragraphs A1-A14, wherein the traction splint is configured to apply traction to the patient's limb when a/the fraction mechanism is engaged by a/the user adjacent the proximal end region of the traction splint.

A16. The traction splint of any of paragraphs A1-A15, wherein the proximal strap is configured to be selectively rotated with respect to the inner member such that the proximal strap is rotatable in a plane, the plane being at least substantially perpendicular to a cross-sectional plane defined by the cross-sectional area of the inner member and the outer member.

A16.1. The traction splint of paragraph A16, wherein the entirety of the proximal strap is configured to be selectively rotated with respect to the inner member.

A16.2. The traction splint of any of paragraphs A1-A16.1, wherein the proximal strap is configured to be selectively rotated with respect to the inner member between a right-limb orientation and a left-limb orientation, wherein, in the right-limb orientation, the traction splint is configured to be secured to a/the patient's right limb, and wherein, in the left-limb orientation, the traction splint is configured to be secured to a/the patient's left limb.

A16.3. The traction splint of paragraph A16.2, wherein in the right-limb orientation the traction splint is configured so that the inner member and the outer member are secured against a selected portion of the patient's right limb.

A16.4. The traction splint of paragraph A16.2 or A16.3, wherein in the left-limb orientation the traction splint is configured so that the inner member and the outer member are secured against a selected portion of the patient's left limb.

A16.4. The traction splint of paragraph A16.3 or A16.4, wherein the selected portion is a lateral portion.

A16.6. The traction splint of any of paragraphs A16.2-A16.5, wherein, in the right-limb orientation, a proximal strap fastener of the proximal strap is positioned adjacent an anterior portion of the patient's right limb and/or adjacent a lateral portion of the patient's right limb, and wherein the proximal strap is configured to be secured around the patient's right limb by traveling posteriorly from the inner member towards a medial portion of the patient's right limb and then be secured via the proximal strap fastener.

A16.7. The traction splint of any of paragraphs A16.2-A16.6, wherein, in the left-limb orientation, a/the proximal strap fastener of the proximal strap is positioned adjacent an anterior portion of the patient's left limb and/or adjacent a lateral portion of the patient's left limb, and wherein the proximal strap is configured to be secured around the patient's left limb by traveling posteriorly from the inner member towards a medial portion of the patient's left limb and then be secured via the proximal strap fastener.

A17. The traction splint of any of paragraphs A16-A16.7, wherein the proximal strap is rotatable at least 90 degrees, at least 180 degrees, and/or at least 360 degrees in a/the plane.

A17.1. The traction splint of any of paragraphs A1-A17, wherein a/the proximal strap fastener is configured to be selectively and reversibly rotated with respect to the inner member to a/the left-limb orientation and to a/the right-limb orientation, wherein, in the right-limb orientation, the traction splint is configured for securement to a/the patient's right limb, wherein, in the left-limb orientation, the traction splint is configured for securement to a/the patient's left limb.

A18. The traction splint of any of paragraphs A1-A17.1, further comprising a proximal strap connector configured to couple the proximal strap to the inner member.

A19. The traction splint of paragraph A18, wherein the proximal strap connector comprises a pin, a grommet, an eyelet, a rivet, and/or a bolt.

A20. The traction splint of paragraph A18 or A19, wherein the proximal strap connector is configured to permit free rotation of the entire proximal strap with respect to the inner member.

A20.1. The traction splint of any of paragraphs A18-A20, wherein the proximal strap connector comprises one or more fasteners.

A20.2. The fraction splint of any of paragraphs A18-A20.1, wherein the proximal strap connector comprises a first fastening component and a second fastening component, wherein the first fastening component is at least substantially stationary with respect to the inner member, and wherein the second fastening component is configured to selectively rotate about the first fastening component.

A20.3. The fraction splint of any of paragraphs A18-A20.2, wherein the proximal strap connector is configured to permit free rotation of a/the entire proximal strap fastener with respect to the inner member.

A21. The traction splint of any of paragraphs A1-A20.3, wherein the distal strap is configured to be selectively rotated with respect to the outer member such that the distal strap is rotatable in a/the plane, the plane being at least substantially perpendicular to a/the cross-sectional plane defined by the cross-sectional area of the inner member and the outer member.

A21.1. The traction splint of paragraph A21, wherein the entirety of the distal strap is configured to be selectively rotated with respect to the outer member.

A21.2. The traction splint of any of paragraphs A1-A21.1, wherein the distal strap is configured to be selectively rotated with respect to the outer member between a/the right-limb orientation and a/the left-limb orientation, wherein, in the right-limb orientation, the fraction splint is configured to be secured to a/the patient's right limb, and wherein, in the left-limb orientation, the traction splint is configured to be secured to a/the patient's left limb.

A21.3. The traction splint of paragraph A21.2, wherein, in the right-limb orientation, a distal strap fastener of the distal strap is positioned adjacent an anterior portion of the patient's right limb and/or adjacent a lateral portion of the patient's right limb, and wherein the distal strap is configured to be secured around the patient's right limb by traveling posteriorly from the outer member towards a medial portion of the patient's right limb and then be secured via the distal strap fastener.

A21.4. The traction splint of paragraph A21.2 or A21.3, wherein, in the left-limb orientation, a/the distal strap fastener of the distal strap is positioned adjacent an anterior portion of the patient's left limb and/or adjacent a lateral portion of the patient's left limb, and wherein the distal strap is configured to be secured around the patient's left limb by traveling posteriorly from the outer member towards a medial portion of the patient's left limb and then be secured via the distal strap fastener.

A22. The traction splint of any of paragraphs A21-A21.4, wherein the distal strap is rotatable at least 90 degrees, at least 180 degrees, and/or at least 360 degrees in the plane.

A22.1. The fraction splint of any of paragraphs A1-A22, wherein a/the distal strap fastener is configured to be selectively and reversibly rotated with respect to the outer member to a/the left-limb orientation and to a/the right-limb orientation, wherein, in the right-limb orientation, the traction splint is configured for securement to a/the patient's right limb, wherein, in the left-limb orientation, the traction splint is configured for securement to a/the patient's left limb.

A23. The traction splint of any of paragraphs A1-A22.1, further comprising a distal strap connector configured to couple the distal strap to the outer member.

A24. The traction splint of paragraph A23, wherein the distal strap connector comprises a pin, a grommet, an eyelet, a rivet, and/or a bolt.

A25. The traction splint of paragraph A23 or A24, wherein the distal strap connector is configured to permit free rotation of the entire distal strap with respect to the outer member.

A25.1. The traction splint of any of paragraphs A23-A25, wherein the distal strap connector comprises one or more fasteners.

A25.2. The traction splint of any of paragraphs A23-A25.1, wherein the distal strap connector comprises a third fastening component and a fourth fastening component, wherein the third fastening component is at least substantially stationary with respect to the outer member, and wherein the fourth fastening component is configured to selectively rotate about the third fastening component.

A25.3. The traction splint of any of paragraphs A23-A25.2, wherein the distal strap connector is configured to permit free rotation of a/the entire distal strap fastener with respect to the outer member.

A26. The traction splint of any of paragraphs A1-A25.3, wherein the inner member is at least substantially non-rotatable about a longitudinal axis of the traction splint.

A27. The traction splint of any of paragraphs A1-A26, wherein the inner member is at least substantially non-rotatable with respect to the outer member.

A28. The traction splint of any of paragraphs A3-A27, wherein the inner member is at least substantially non-rotatable with respect to the middle member.

A29. The traction splint of any of paragraphs A3-A28, wherein the middle member is at least substantially non-rotatable with respect to the outer member.

A30. The traction splint of any of paragraphs A1-A29, wherein the traction splint comprises an anti-rotation feature configured to prevent rotation of the inner member with respect to the outer member.

A31. The traction splint of any of paragraphs A3-A30, wherein the traction splint comprises an/the anti-rotation feature configured to prevent rotation of the middle member with respect to the outer member.

A32. The traction splint of paragraph A31, wherein the anti-rotation feature is further configured to prevent separation of the middle member from the outer member.

A33. The traction splint of any of paragraphs A30-A32, wherein the anti-rotation feature comprises a longitudinally-extending slot formed in the outer member.

A34. The fraction splint of paragraph A33, wherein the anti-rotation feature comprises a pin that extends at least partially through the longitudinally-extending slot.

A35. The traction splint of paragraph A34, wherein the pin is coupled to the inner member.

A36. The traction splint of paragraph A34 or A35, wherein the pin is formed integrally with the inner member.

A36.1. The traction splint of paragraph A35 or A36, wherein the pin is configured to travel longitudinally along the longitudinally-extending slot as the inner member is moved with respect to the outer member.

A37. The traction splint of paragraph A3 and A34, wherein the pin is coupled to the middle member.

A38. The traction splint of paragraph A3 and A34, wherein the pin is formed integrally with the middle member.

A39. The traction splint of paragraph A37 or A38, wherein the pin is configured to travel longitudinally along the longitudinally-extending slot as the middle member is moved with respect to the outer member.

A40. The traction splint of any of paragraphs A1-A39, wherein, in the collapsed configuration, the proximal end region of the traction splint is located a first distance from the distal end region of the traction splint, wherein, in the extended configuration, the proximal end region of the traction splint is located a second distance from the distal end region of the traction splint, and wherein the second distance is greater than the first distance.

A41. The traction splint of any of paragraphs A1-A40, further comprising a tourniquet portion coupled to the distal strap, the tourniquet portion being configured to be sufficiently constricted around a portion of the patient's limb to at least partially occlude blood flow through the portion of the patient's limb.

A41.1. The traction splint of paragraph A41, wherein the tourniquet portion comprises a ratchet mechanism configured to tighten the distal strap sufficiently enough such that it at least partially occludes blood flow through the portion of the patient's limb.

A42. The traction splint of any of paragraphs A1-A41.1, wherein a/the tourniquet portion is coupled to the proximal strap, wherein the tourniquet portion is configured to be sufficiently constricted around a/the portion of the patient's limb to at least partially occlude blood flow through the portion of the patient's limb.

A42.1. The traction splint of paragraph A42, wherein the tourniquet portion comprises a/the ratchet mechanism configured to tighten the proximal strap sufficiently enough such that it at least partially occludes blood flow through the portion of the patient's limb.

A43. The traction splint of any of paragraphs A1-A42.1, further comprising a/the proximal strap fastener configured to secure the proximal strap around the patient's limb such that the proximal strap forms a proximal loop around the patient's limb.

A43.1. The traction splint of paragraph A43, wherein the proximal strap fastener comprises a first fastener part and a second fastener part configured to engage with one another in order to secure the proximal strap in the proximal loop around the patient's limb.

A43.2. The traction splint of paragraph A43.1, wherein the first fastener part comprises a male buckle portion, and the second fastener part comprises a female buckle portion configured to receive the male buckle portion, thereby securing the proximal strap in the proximal loop around the patient's limb.

A43.3. The traction splint of any of paragraphs A43-A43.2, wherein the proximal strap is configured to form the proximal loop around the patient's limb when the proximal strap fastener is engaged, wherein the traction splint is configured such that a circumference of the proximal loop may be selectively increased and decreased.

A43.4. The fraction splint of any of paragraphs A43-A43.3, wherein the proximal strap fastener comprises a clip, a buckle, a clasp, a button, a snap, a D-ring, a ladderlock, a Velcro® portion, a cam buckle, a lever buckle, and/or a side-squeeze buckle.

A43.5. The traction splint of any of paragraphs A1-A43.4, wherein the proximal strap is configured to secure the traction splint to the patient's limb adjacent the proximal end region of the traction splint by forming a/the proximal loop around the patient's limb with the proximal strap and securing the proximal loop with a/the proximal strap fastener.

A44. The traction splint of any of paragraphs A43-A43.5, further comprising a proximal padding portion coupled to the proximal strap, wherein the proximal padding portion is configured to be positioned between the patient's limb and the proximal strap fastener, the proximal padding portion being configured to provide cushioning to the patient's limb.

A45. The traction splint of any of paragraphs A1-A44, further comprising a/the distal strap fastener configured to secure the distal strap around the patient's limb such that the distal strap forms a distal loop around the patient's limb.

A45.1. The traction splint of paragraph A45, wherein the distal strap fastener comprises a clip, a buckle, a clasp, a button, a snap, a D-ring, a ladderlock, a Velcro® portion, a cam buckle, a lever buckle, and/or a side-squeeze buckle.

A45.2. The traction splint of paragraph A45 or A45.1, wherein the distal strap fastener comprises a third fastener part and a fourth fastener part configured to engage with one another in order to secure the distal strap in the distal loop around the patient's limb.

A45.3. The traction splint of paragraph A45.2, wherein the third fastener part comprises a male buckle portion, and the fourth fastener part comprises a female buckle portion configured to receive the male buckle portion, thereby securing the distal strap in the distal loop around the patient's limb.

A45.4. The traction splint of any of paragraphs A45-A45.3, wherein the distal strap is configured to form the distal loop around the patient's limb when the distal strap fastener is engaged, wherein the traction splint is configured such that a circumference of the distal loop may be selectively increased and decreased.

A45.5. The traction splint of any of paragraphs A1-A45.4, wherein the distal strap is configured to secure the traction splint to the patient's limb adjacent the distal end region of the traction splint by forming a/the distal loop around the patient's limb with the distal strap and securing the distal loop with a/the distal strap fastener.

A46. The traction splint of any of paragraphs A45-A45.5, further comprising a distal padding portion coupled to the distal strap, wherein the distal padding portion is configured to be positioned between the patient's limb and the distal strap fastener, the distal padding portion being configured to provide cushioning to the patient's limb.

A47. The traction splint of any of paragraphs A1-A46, wherein the proximal strap is at least partially elastic.

A48. The traction splint of any of paragraphs A1-A47, wherein the proximal strap comprises a rubberized portion.

A49. The traction splint of paragraph A48, wherein the rubberized portion comprises a plurality of embedded elastic fibers integrated into the proximal strap.

A50. The traction splint of any of paragraphs A1-A49, wherein the distal strap is at least partially elastic.

A51. The traction splint of any of paragraphs A1-A50, wherein the distal strap comprises a rubberized portion.

A52. The traction splint of paragraph A51, wherein the rubberized portion comprises a plurality of embedded elastic fibers integrated into the distal strap.

A53. The traction splint of any of paragraphs A1-A52, further comprising a middle strap positioned between the proximal strap and the distal strap, the middle strap being configured to secure the traction splint to the patient's limb.

A54. The traction splint of paragraph A53, wherein the middle strap is configured to be selectively moved in a longitudinal direction with respect to the inner member and the outer member.

A55. The traction splint of paragraph A53 or A54 wherein the middle strap comprises a middle strap fastener configured to secure the middle strap in a middle loop around the patient's limb.

A56. The traction splint of any of paragraphs A1-A55, wherein the traction splint is configured to be lightweight and portable.

A57. The traction splint of any of paragraphs A1-A56, wherein the traction splint is configured to be stored in the collapsed configuration.

A58. The traction splint of any of paragraphs A1-A57, wherein the traction splint is configured to be ready for securement to the patient's limb after extending the fraction splint from the collapsed configuration towards the extended configuration, to a desired length.

A59. The traction splint of any of paragraphs A1-A58, wherein the traction splint is configured to be selectively and reversibly adjusted in length such that it may be appropriately sized for both an adult patient and a pediatric patient.

A60. The traction splint of any of paragraphs A1-A59, wherein the traction splint is configured to be selectively and reversibly adjusted in length such that is may be appropriately sized for use on both a patient's arm and a patient's leg.

A61. The traction splint of any of paragraphs A1-A60, wherein the proximal strap is configured to be positioned around a patient's thigh, adjacent a patient's pelvis.

A62. The traction splint of any of paragraphs A1-A61, wherein the distal strap is configured to be positioned around a patient's lower leg, adjacent and distal to a patient's knee.

A63. The traction splint of any of paragraphs A1-A62, wherein the inner member is a non-foldable inner member.

A64. The traction splint of any of paragraphs A1-A63, wherein the outer member is a non-foldable outer member.

A65. The traction splint of any of paragraphs A1-A64, wherein the inner member and the outer member are at least substantially concentric.

A66. The traction splint of any of paragraphs A1-A65, wherein the inner member, a/the middle member, and the outer member are at least substantially concentric.

A67. The traction splint of any of paragraphs A1-A66, wherein the traction splint is configured to be secured to the patient's limb such that the inner member and the outer member are positioned adjacent a/the lateral portion of the patient's limb.

A68. The traction splint of any of paragraphs A1-A67, wherein the outer member and the inner member are at least substantially circular in cross-section.

A69. The traction splint of any of paragraphs A1-A68, wherein a/the middle member is at least substantially circular in cross-section, wherein the middle member is at least partially positioned circumferentially between the inner member and the outer member.

A70. The traction splint of any of paragraphs A1-A67, wherein the outer member and the inner member are non-circular in cross-section.

A71. The traction splint of paragraph A70, wherein the outer member and the inner member are at least substantially polygonal in cross-section.

A72. The traction splint of paragraph A70 or A71, wherein a/the middle member is non-circular in cross-section, wherein the middle member is at least partially positioned circumferentially between the inner member and the outer member.

A73. The traction splint of paragraph A72, wherein the middle member is at least substantially polygonal in cross-section.

B1. A method, comprising:

providing the traction splint of any of paragraphs A1-A73; and securing the traction splint to a patient's limb.

B2. The method of paragraph B1, wherein the securing the traction splint to the patient's limb comprises looping the proximal strap around the patient's limb, fastening the proximal strap via a/the proximal strap fastener, and tightening the proximal strap around the patient's limb.

B3. The method of paragraph B1 or B2, wherein the securing the fraction splint to the patient's limb comprises looping the distal strap around the patient's limb, fastening the distal strap via a/the distal strap fastener, and tightening the distal strap around the patient's limb.

B4. The method of any of paragraphs B1-B3, wherein the securing the traction splint comprises positioning the proximal strap around the patient's thigh, adjacent the patient's pelvis.

B5. The method of any of paragraphs B1-B4, wherein the securing the traction splint comprises positioning the distal strap around a/the patient's lower leg, adjacent and distal to a/the patient's knee.

B6. The method of any of paragraphs B1-B5, wherein the securing the traction splint comprises positioning a female buckle portion of a/the proximal strap fastener on a patient's anterior thigh.

B7. The method of any of paragraphs B1-B6, further comprising extending the traction splint from the collapsed configuration towards the extended configuration.

B7.1. The method of paragraph B7, further comprising at least temporarily retaining the traction splint in a respective position between the collapsed configuration and the extended configuration, inclusive.

B8. The method of paragraph B7 or B7.1, wherein the extending the traction splint comprises selectively and reversibly adjusting a/the length of the traction splint in accordance with a size of the patient's limb.

B9. The method of paragraph B7 or B8, wherein the extending the traction splint comprises increasing a distance between the proximal end region of the traction splint and the distal end region of the fraction splint.

B10. The method of any of paragraphs B7-B9, wherein the extending the traction splint comprises longitudinally sliding the inner member with respect to the outer member.

B11. The method of any of paragraphs B7-B10, wherein the extending the traction splint comprises longitudinally sliding the inner member with respect to a/the middle member at least partially positioned between the inner member and the outer member.

B11.1. The method of paragraph B11, wherein the extending the traction splint comprises longitudinally sliding the inner member with respect to the middle member, substantially without rotating the inner member with respect to the middle member.

B12. The method of any of paragraphs B7-B11.1, wherein the extending the traction splint comprises longitudinally sliding a/the middle member with respect to the outer member.

B12.1. The method of any of paragraphs B1-B12, wherein the traction splint comprises an/the anti-rotation feature configured to prevent rotation of a/the middle member with respect to the outer member.

B13. The method of any of paragraphs B7-B12.1, wherein the extending the traction splint comprises engaging a/the first adjustment mechanism, thereby permitting extension of the inner member with respect to the outer member.

B14. The method of any of paragraphs B7-B13, wherein the extending the traction splint comprises engaging a/the second adjustment mechanism, thereby permitting extension of a/the middle member with respect to the outer member.

B15. The method of any of paragraphs B7-B14, wherein the extending the traction splint comprises depressing a/the plunger through a respective adjustment hole formed in the outer member, and moving a/the middle member with respect to the outer member until the plunger is positioned such that it extends through a different respective adjustment hole of the outer member.

B16. The method of any of paragraphs B7-B15, wherein the extending the traction splint comprises loosening a/the nut portion of a/the first adjustment mechanism relative to a/the threaded portion of the first adjustment mechanism.

B17. The method of any of paragraphs B1-B16, further comprising applying traction to the patient's limb using the traction splint.

B18. The method of paragraph B17, wherein the applying traction comprises applying a/the tension force to a/the external portion of a/the traction cord extending from the inner member adjacent the proximal end region of the traction splint.

B19. The method of paragraph B18, wherein the applying traction comprises tightening a/the nut portion of the traction splint relative to a/the threaded portion of a/the first adjustment mechanism, while holding the traction cord taut, thereby sustaining tension on the traction cord and securing the traction splint in a position in which it applies traction to the patient's limb.

B20. The method of any of paragraphs B1-B19, further comprising at least partially occluding blood flow to a portion of the patient's limb by tightening a/the tourniquet portion of the traction splint.

B21. The method of any of paragraphs B1-B20, further comprising rotating the proximal strap and the distal strap from a/the right-limb orientation to a/the left-limb orientation, or vice versa, wherein, in the right-limb orientation, the traction splint is configured to be secured to a/the patient's right limb, and wherein, in the left-limb orientation, the traction splint is configured to be secured to a/the patient's left limb.

B22. The method of paragraph B21, wherein the rotating the proximal strap and the distal strap comprises rotating the proximal strap approximately 180 degrees with respect to the inner member and rotating the distal strap approximately 180 degrees with respect to the outer member, wherein the proximal strap and the distal strap are rotated in a/the plane, the plane being at least substantially perpendicular to a/the cross-sectional plane defined by a/the cross-sectional area of the inner member and the outer member.

B23. The method of any of paragraphs B1-B22, further comprising rotating at least one of (1) a/the proximal strap fastener and the entire proximal strap with respect to the inner member and (2) a/the distal strap fastener and the entire distal strap with respect to the outer member, such that the traction splint is positioned in one of a/the left-limb orientation and a/the right-limb orientation, wherein, in the right-limb orientation, the traction splint is configured for securement to a/the patient's right limb, wherein, in the left-limb orientation, the traction splint is configured for securement to a/the patient's left limb.

B23.1. The method of paragraph B23, wherein the proximal strap, the proximal strap fastener, the distal strap, and/or the distal strap fastener are positioned in one of the left-limb orientation and the right-limb orientation.

B24. The method of any of paragraphs B1-B23.1, further comprising collapsing the traction splint towards the collapsed configuration.

B25. The method of paragraph B24, wherein the collapsing the traction splint comprises decreasing a/the distance between the proximal end region of the traction splint and the distal end region of the traction splint.

INDUSTRIAL APPLICABILITY

The traction splints and methods disclosed herein are applicable to the medical and first aid fields, such as military first aid, outdoor first aid, and/or emergency response. They may also be applied in hospital emergency departments or wards for preoperative fracture stabilization and/or hemostasis.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such claims should be understood to include incorporation of one or more such elements, neither requiring nor excluding two or more such elements.

Applicant reserves the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. A traction splint configured to apply traction to a patient's limb, the traction splint comprising:
    an outer member having a distal strap coupled thereto via a distal strap connector, the distal strap being configured to secure the traction splint to the patient's limb adjacent a distal end region of the traction splint;
    a middle member nested at least partially within the outer member;
    an inner member nested at least partially within the middle member and having a proximal strap coupled thereto via a proximal strap connector, the proximal strap being configured to secure the traction splint to the patient's limb adjacent a proximal end region of the traction splint, wherein at least a portion of the middle member is positioned between the inner member and the outer member;
    a first adjustment mechanism configured to selectively allow movement of the inner member with respect to the middle member;
    a second adjustment mechanism configured to selectively allow movement of the middle member with respect to the outer member;
    a traction mechanism having a traction cord, wherein an external portion of the traction cord extends from the inner member adjacent the proximal end region of the traction splint, wherein the traction mechanist configured to apply traction such that the inner member and the outer member are pressed away from one another when a tension force is applied to the external portion of the traction cord;
    a proximal strap fastener configured to secure the proximal strap in a proximal loop around the patient's limb, wherein the traction splint is configured such that a first circumference of the proximal loop may be selectively increased and decreased, wherein the proximal strap fastener is configured to be selectively rotated with respect to the inner member and with respect to the proximal strap, between a right-limb orientation and a left-limb orientation; and
    a distal strap fastener configured to secure the distal strap in a distal loop around the patient's limb, wherein the traction splint is configured such that a second circumference of the distal loop may be selectively increased and decreased, and wherein the distal strap fastener is configured to be selectively rotated with respect to the outer member and with respect to the distal strap, between the right-limb orientation and the left-limb orientation,
    wherein the traction splint is configured to be selectively and reversibly extended from a collapsed configuration towards an extended configuration by sliding the inner member in a longitudinal direction with respect to the middle member and by sliding the middle member in the longitudinal direction with respect to the outer member, wherein a first distance between the proximal end region of the traction splint and the distal end region of the traction splint in the collapsed configuration is less than a second distance between the proximal end region of the traction splint and the distal end region of the traction splint in the extended configuration,
    wherein the proximal strap is configured to be selectively rotated, with respect to the inner member and via the proximal strap connector, between the right-limb orientation and the left-limb orientation, wherein, in the right-limb orientation, the traction splint is configured to be secured to the patient's right limb, and wherein, in the left-limb orientation, the traction splint is configured to be secured to the patient's left limb, and wherein the distal strap is configured to be selectively rotated, with respect to the outer member and via the distal strap connector, between the right-limb orientation and the left-limb orientation.

2. The traction splint of claim 1, wherein the traction splint further comprises an anti-rotation feature configured to prevent rotation of the middle member with respect to the outer member.

3. The traction splint according to claim 2, wherein the inner member is at least substantially non-rotatable with respect to the middle member, and wherein the middle member is at least substantially non-rotatable with respect to the outer member.

4. The traction splint according to claim 2, wherein the anti-rotation feature is further configured to prevent separation of the middle member from the outer member.

5. The traction splint according to claim 2, wherein the anti-rotation feature comprises a longitudinally-extending slot formed in the outer member and a pin coupled to the middle member that extends at least partially through the longitudinally-extending slot, wherein the pin is configured to travel longitudinally along the longitudinally-extending slot as the middle member is moved with respect to the outer member.

6. The traction splint according to claim 2, further comprising a tourniquet portion coupled to the distal strap, the tourniquet portion being configured to be sufficiently constricted around a portion of the patient's limb to at least partially occlude blood flow through the portion of the patient's limb.

7. The traction splint according to claim 1, wherein the proximal strap is configured to be selectively rotated at least substantially in a plane of rotation, the plane of rotation being at least substantially perpendicular to a cross-sectional plane that is perpendicular to a longitudinal axis of the inner member and the outer member, and wherein the distal strap is configured to be selectively rotated at least substantially in the plane of rotation.

8. The traction splint according to claim 7, wherein the entire proximal strap is configured to be selectively rotated at least 180 degrees in the plane of rotation, and wherein the entire distal strap is configured to be selectively rotated at least 180 degrees in the plane of rotation.

9. The traction splint according to claim 1, wherein the first adjustment mechanism comprises a post extending through the inner member and the middle member and a nut portion positioned adjacent an outer surface of the middle member, wherein the post comprises a head portion positioned adjacent the outer surface of the middle member, and wherein the first adjustment mechanism is configured such that tightening the nut portion relative to a threaded portion of the post is configured to prevent movement of the inner member with respect to the middle member.

10. The traction splint according to claim 9, wherein the first adjustment mechanism is configured such that tightening the nut portion relative to the threaded portion locks the traction cord, such that the traction splint sustains a traction force on the patient's limb.

11. The traction splint according to claim 1, wherein the distal strap fastener comprises a D-ring configured to secure the distal strap in the distal loop around the patient's limb.

12. The traction splint according to claim 11, wherein the proximal strap fastener is configured to be selectively rotated at least substantially in a plane of rotation, the plane of rotation being at least substantially perpendicular to a cross-sectional plane that is perpendicular to a longitudinal axis of the inner member and the outer member, and wherein the distal strap fastener is configured to be selectively rotated at least substantially in the plane of rotation.

13. The traction splint according to claim 1, wherein each of the proximal strap and the proximal strap fastener is configured to be selectively rotated at least substantially in a plane of rotation, the plane of rotation being at least substantially perpendicular to a cross-sectional plane defined by a cross-sectional area of the inner member and the outer member, wherein the cross-sectional plane is perpendicular to a longitudinal axis of the inner member and the outer member, and wherein each of the distal strap and the distal strap fastener is configured to be selectively rotated at least substantially in the plane of rotation.

14. The traction splint according to claim 13, wherein the proximal strap fastener is configured to be selectively rotated via the proximal strap connector, and wherein the distal strap fastener is configured to be selectively rotated via the distal strap connector.

15. The traction splint according to claim 1, wherein the proximal strap connector and the distal strap connector each comprise one or more fastening components selected from the group consisting of a pin, a grommet, an eyelet, a rivet, and a bolt.

16. The traction splint according to claim 1, wherein the proximal strap connector comprises a first fastening component and a second fastening component, wherein the distal strap connector comprises a third fastening component and a fourth fastening component, wherein the first fastening component is at least substantially stationary with respect to the inner member when the proximal strap is selectively rotated with respect to the inner member between the right-limb orientation and the left-limb orientation, wherein the third fastening component is at least substantially stationary with respect to the outer member when the distal strap is selectively rotated with respect to the outer member between the right-limb orientation and the left-limb orientation, wherein the second fastening component is configured to selectively rotate about the first fastening component, and wherein the fourth fastening component is configured to selectively rotate about the third fastening component.

17. The traction splint according to claim 7, wherein the proximal strap fastener comprises a first fastener part and a second fastener part configured to engage with one another in order to secure the proximal strap in the proximal loop around the patient's limb.

18. The traction splint according to claim 1, wherein at least one of the proximal strap and the distal strap comprises a plurality of embedded elastic fibers.

19. The traction splint according to claim 1, wherein the second adjustment mechanism comprises a plunger, wherein the outer member comprises a plurality of adjustment holes, wherein the plunger is spring-biased to extend through a respective one of the plurality of adjustment holes when the plunger is not depressed, and wherein the traction splint is configured to be selectively and reversibly extended towards the extended configuration by depressing the plunger and sliding the middle member longitudinally with respect to the outer member until the middle member is positioned such that the plunger extends through a desired respective adjustment hole of the outer member, thereby preventing further longitudinal sliding of the middle member with respect to the outer member until the plunger is again depressed.

20. The traction splint according to claim 1, wherein the traction mechanism comprises a pulley, wherein the traction cord follows a cord path that travels around a post of the first adjustment mechanism, wherein the post extends through the inner member.

21. The traction splint according to claim 1, further comprising a tourniquet portion coupled to the distal strap, the tourniquet portion being configured to be sufficiently constricted around a portion of the patient's limb to at least partially occlude blood flow through the portion of the patient's limb.

22. The traction splint according to claim 1, wherein, in the right-limb orientation, the traction splint is configured to be secured to the patient's limb such that the inner member, the middle member, and the outer member are positioned adjacent a lateral portion of the patient's right limb, and wherein, in the left-limb orientation, the traction splint is configured to be secured to the patient's limb such that the inner member, the middle member, and the outer member are positioned adjacent a lateral portion of the patient's left limb.

23. The traction splint according to claim 1, wherein the proximal strap connector comprises a first fastening component and a second fastening component, wherein the distal strap connector comprises a third fastening component and a fourth fastening component, wherein the first fastening component is at least substantially stationary with respect to the inner member when the proximal strap is selectively rotated with respect to the inner member between the right-limb orientation and the left-limb orientation, wherein the third fastening component is at least substantially stationary with respect to the outer member when the distal strap is selectively rotated with respect to the outer member between the right-limb orientation and the left-limb orientation, wherein the second fastening component is configured to selectively rotate about the first fastening component, wherein the fourth fastening component is configured to selectively rotate about the third fastening component, wherein the proximal strap is configured to be selectively rotated at least substantially in a plane of rotation, the plane of rotation being at least substantially perpendicular to a cross-sectional plane that is perpendicular to a longitudinal axis of the inner member and the outer member, and wherein the distal strap is configured to be selectively rotated at least substantially in the plane of rotation.

24. The traction splint according to claim 1, wherein, in the right-limb orientation, the traction splint is configured to apply traction to the patient's right limb such that the proximal strap fastener and the distal strap fastener are each positioned adjacent a first anterior portion and a first lateral portion of the patient's right limb, and wherein, in the left-limb orientation, the traction splint is configured to apply traction to the patient's left limb such that the proximal strap fastener and the distal strap fastener are each positioned adjacent a second anterior portion and a second lateral portion of the patient's left limb.

* * * * *

UNITED STATES PATENT AND TRADEMARK OFFICE
CERTIFICATE OF CORRECTION

PATENT NO. : 10,517,750 B2
APPLICATION NO. : 14/949569
DATED : December 31, 2019
INVENTOR(S) : Samuel Slishman Page 1 of 1

It is certified that error appears in the above-identified patent and that said Letters Patent is hereby corrected as shown below:

In the Claims

Claim 1, Column 36, Line 22, after "traction" please delete "mechanist" and insert --mechanism is-- therefor.

Claim 17, Column 38, Line 41, after "according to claim" please delete "7" and insert --1-- therefor.

Signed and Sealed this
Eighteenth Day of February, 2020

Andrei Iancu
*Director of the United States Patent and Trademark Office*